(12) United States Patent
Srinivasan et al.

(10) Patent No.: US 11,220,735 B2
(45) Date of Patent: Jan. 11, 2022

(54) METHODS FOR CONTROLLING PHYSICAL VAPOR DEPOSITION METAL FILM ADHESION TO SUBSTRATES AND SURFACES

(71) Applicant: MEDTRONIC MINIMED, INC., Northridge, CA (US)

(72) Inventors: Akhil Srinivasan, Sherman Oaks, CA (US); Yifei Wang, Sunnyvale, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 502 days.

(21) Appl. No.: 15/892,172

(22) Filed: Feb. 8, 2018

(65) Prior Publication Data

US 2019/0242010 A1 Aug. 8, 2019

(51) Int. Cl.
| | | |
|---|---|---|
| *C23C 14/00* | (2006.01) |
| *C23C 14/02* | (2006.01) |
| *C23C 14/06* | (2006.01) |
| *C23C 14/14* | (2006.01) |
| *C23C 14/18* | (2006.01) |
| *C23C 14/20* | (2006.01) |
| *C23C 14/30* | (2006.01) |
| *C23C 14/34* | (2006.01) |

(Continued)

(52) U.S. Cl.
CPC ...... *C23C 14/0005* (2013.01); *A61B 5/14532* (2013.01); *C23C 14/025* (2013.01); *C23C 14/06* (2013.01); *C23C 14/14* (2013.01); *C23C 14/18* (2013.01); *C23C 14/20* (2013.01); *C23C 14/30* (2013.01); *C23C 14/34* (2013.01); *C23C 14/545* (2013.01); *G01N 27/327* (2013.01); *G01N 27/4115* (2013.01)

(58) Field of Classification Search
CPC ... C23C 14/34; C23C 14/0005; C23C 14/545; C23C 14/18; C23C 14/30; C23C 14/025; C23C 14/14; C23C 14/0042; C23C 14/06; C23C 14/20; A61B 5/14532; A61B 5/14865; A61B 2562/12; A61B 2562/125; G01N 27/30; G01N 27/3271; G01N 27/327; G01N 27/4115
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |

(Continued)

OTHER PUBLICATIONS

Yang Y.; Jia, H.; Zhang, Z.; Shen, H.; Hu, A.; Wang, Y. Transformations in sputter-deposited thin films of NiTi shape memory alloy. Materials Letters, Feb. 1995, p. 137-140. 1995 (Year: 1995).*

(Continued)

*Primary Examiner* — Michael A Band
(74) *Attorney, Agent, or Firm* — Gates & Cooper LLP

(57) ABSTRACT

A method of depositing of a film on a substrate with controlled adhesion. The method comprises depositing the film including metal, wherein the metal is deposited on the substrate using physical vapor deposition at a pressure that achieves a pre-determined adhesion of the film to the substrate. The pre-determined adhesion allows processing of the film into a device while the film is adhered to the substrate but also allows removal of the device from the substrate.

14 Claims, 32 Drawing Sheets

(51) Int. Cl.
*C23C 14/54* (2006.01)
*G01N 27/327* (2006.01)
*G01N 27/411* (2006.01)
*A61B 5/145* (2006.01)

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,506,767 B2 * | 8/2013 | Johnson ............ A61F 2/82 204/192.12 |
| 9,506,890 B2 * | 11/2016 | Hochstetler ........... G01N 27/00 |
| 2007/0123819 A1 | 5/2007 | Mernoe et al. |
| 2007/0227907 A1 | 10/2007 | Shah et al. |
| 2008/0026473 A1 | 1/2008 | Wang et al. |
| 2010/0160861 A1 | 6/2010 | Causey, III et al. |
| 2011/0152654 A1 | 6/2011 | Wang et al. |
| 2012/0190950 A1 | 7/2012 | Yang et al. |
| 2013/0056144 A1 | 3/2013 | Kotzan et al. |
| 2014/0228660 A1 | 8/2014 | Mujeeb-U-Rahman et al. |
| 2016/0262675 A1 | 9/2016 | Shah et al. |
| 2017/0055892 A1 | 3/2017 | Little et al. |
| 2018/0325430 A1 | 11/2018 | Vaddiraju et al. |
| 2019/0008425 A1 * | 1/2019 | Srinivasan ......... A61B 5/14865 |
| 2019/0239778 A1 * | 8/2019 | Srinivasan ......... A61B 5/14865 |

OTHER PUBLICATIONS

PCT International Search Report & Written Opinion dated Aug. 23, 2019 for PCT Application No. PCT/US2019/016926.
Gulati, R., et al., "Improved metal-dielectric adhesion for interconnect liners of MMICs and ICs: an experimental study", Materials Science and Engineering: B, Dec. 1994, pp. 357-360, vol. 28, Issues 1-3.
PCT International Search Report dated May 16, 2019 for PCT Application No. PCT/US2019/016828.

* cited by examiner

600

| Group | Pressure (mTorr) | Power (kW) | Heat WHEN START (°C) | Time (min) | Gold Thickness (Å) | Adhesion score |
|---|---|---|---|---|---|---|
| 1 | 4 | 1.5 | 120 | 5 | 3703 | 0 |
| 2 | 4 | 0.2 | 120 | 10 | 1270 | 0 |
| 3 | 4 | 1.5 | No heat | 5 | 3712 | 0 |
| 4 | 4 | 0.2 | No heat | 10 | 1209 | 0 |
| 5 | 100 | 1.5 | 120 | 5 | 2304 | 0 |
| 6 | 100 | 0.2 | 120 | 10 | 685 | 3 |
| 7 | 100 | 1.5 | No heat | 5 | 2905 | 10 |
| 8 | 100 | 0.2 | No heat | 10 | 671 | 4 |

FIG. 7E

| Group | Pressure (mTorr) | Power (kW) | Target thickness without Cr (Å) | Time (sec) | Measured thickness without Cr (Å) | Adhesion score |
|---|---|---|---|---|---|---|
| 1 | 55 | 1 | 5000 | 532 | 4942 | 0 |
| 2 | 10 | 0.4 | 1000 | 239 | 1068 | 0 |
| 3 | 10 | 0.4 | 9000 | 2153 | 9232 | 0 |
| 4 | 10 | 1.6 | 1000 | 64 | 965 | 0 |
| 5 | 10 | 1.6 | 9000 | 580 | 8446 | 0 |
| 6 | 100 | 0.4 | 1000 | 700 | 952 | 8.5 |
| 7 | 100 | 0.4 | 9000 | 6000 | 8622 | 10 |
| 8 | 100 | 1.6 | 1000 | 120 | 897 | 8 |
| 9 | 100 | 1.6 | 9000 | 1083 | 10806 | 10 |
| 10 | 55 | 1 | 5000 | 532 | 4848 | 0 |
| 11 | 100 mT, 1.5 kW, 5min then 4mT, 0.2kW, 10min | | | | 3952 | by position! |

FIG. 7F

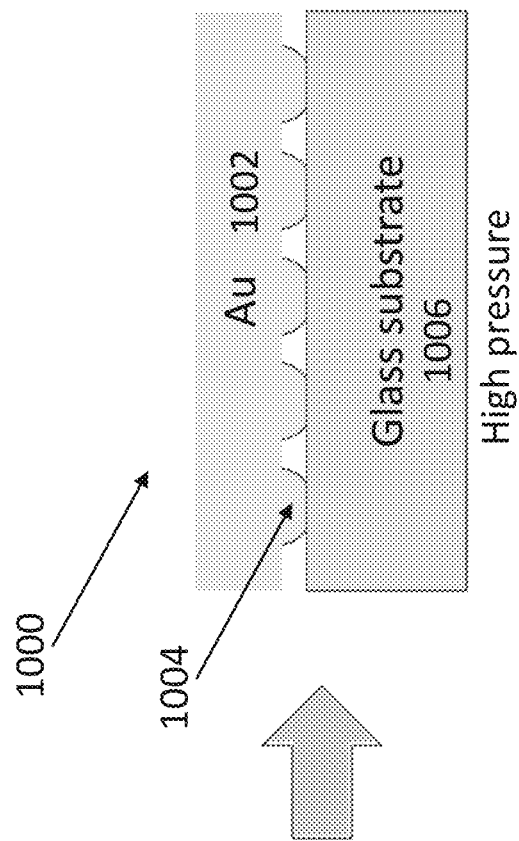
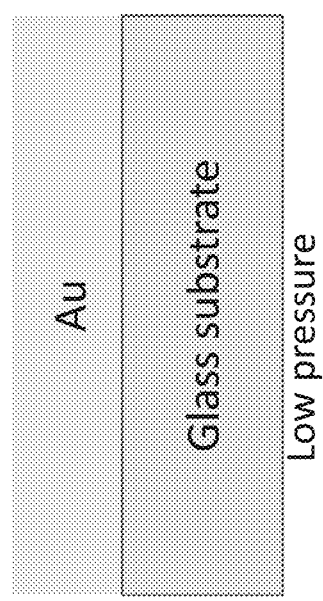
FIG. 8B
FIG. 8A

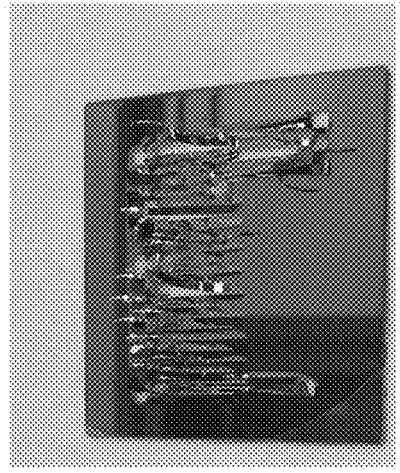
FIG. 10C — 100mT, 0.4W, 8922A
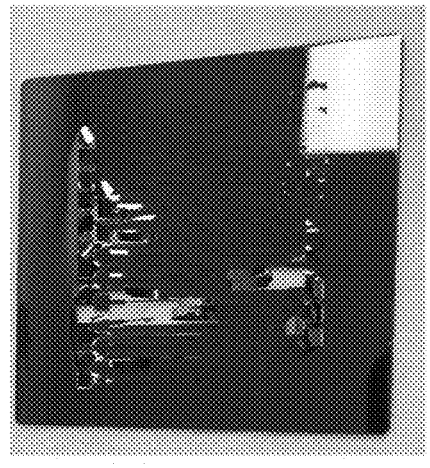
FIG. 10D — 100mT, 1.6W, 10806A
FIG. 10A — 100mT, 0.4W, 952A
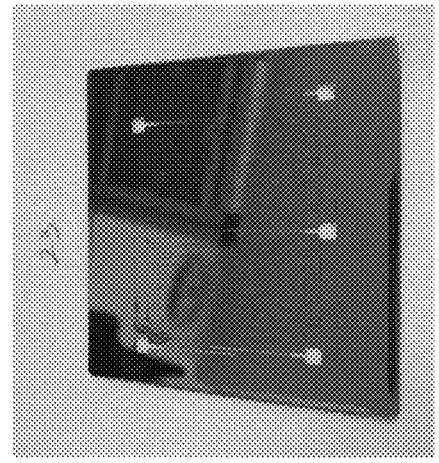
FIG. 10B — 100mT, 1.6W, 897A

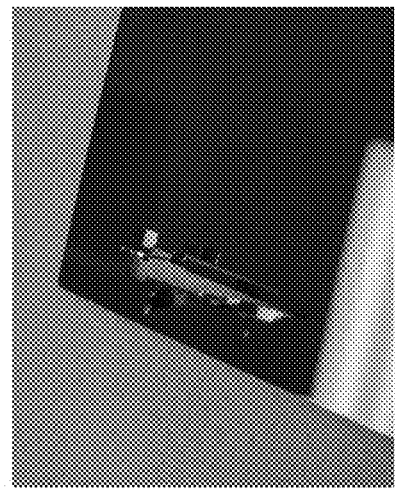
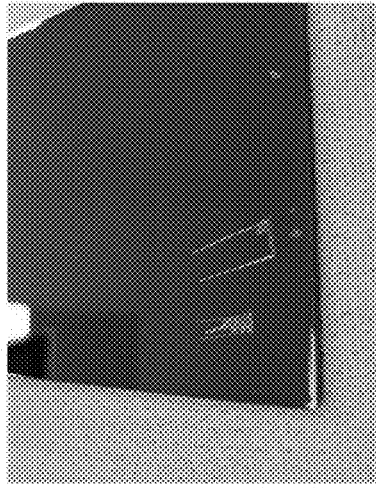
First layer: 100mT, 1.5 kW, 5min
Second layer: 4mT, 0.2 kW, 10min
Adhesion varies as a function of position
FIG. 15A
FIG. 15B
FIG. 15C

METHODS FOR CONTROLLING PHYSICAL VAPOR DEPOSITION METAL FILM ADHESION TO SUBSTRATES AND SURFACES

TECHNICAL FIELD

The invention relates to a method for controlling adhesion of films deposited on a substrate and devices fabricated using the same.

BACKGROUND OF THE INVENTION

Electrochemical sensors are commonly used to detect or measure the concentrations of in vivo analytes, such as glucose. Typically in such analyte sensing systems, an analyte (or a species derived from it) is electro-active and generates a detectable signal at an electrode in the sensor. This signal is then correlated with the presence or concentration of the analyte within a biological sample. In some conventional sensors, an enzyme is provided that reacts with the analyte to be measured, the byproduct of the reaction being qualified or quantified at the electrode. In one conventional glucose sensor, immobilized glucose oxidase catalyzes the oxidation of glucose to form hydrogen peroxide, which is then quantified by amperometric measurements (e.g. change in electrical current) through one or more electrodes.

A variety of electrochemical glucose sensors are multi-layered, comprising electrodes on top of and/or coated by layers of various materials. Multilayered sensors have a number of desirable properties including the fact that the functional properties of such sensors can be tailored by altering certain design parameters (e.g. number of internal layers, layer thickness, electrodes area and architecture etc). However, the inventors of the present invention have found that undesirable interactions between the anode and cathode in conventional sensors degrade sensor performance. What is needed, then, are sensor fabrication methods and electrode structures that reduce or prevent unwanted cathode-anode interactions, thereby improving sensor performance. The present disclosure satisfies this need.

SUMMARY OF THE INVENTION

The present disclosure reports on techniques developed to control adhesion of a metal film through a physical vapor deposition (PVD) process. A variety of PVD parameters were evaluated through multiple Design of Experiments (DOEs). Pressure was unexpectedly and surprisingly discovered to have the largest and most significant impact on adhesion, and controlling and changing the pressure during the PVD the process achieved different levels of adhesion.

In one illustrative embodiment, a method of depositing of a film on a substrate comprises placing a substrate in a PVD chamber; setting a pressure of a gas in the chamber; depositing metal on the substrate using PVD at the pressure; and depositing a film on the metal. The pressure is associated with a pre-determined adhesion of the film to the substrate, the pre-determined adhesion allowing processing (e.g., cutting) of the film into one or more devices while the film is adhered to the substrate and removal of the device from the substrate. In one or more examples the pressure is in a range of 2-250 millitorr (mTorr), the PVD power is in a range of 10 W kilowatts to 100 kilowatts, and the metal comprises a layer having a thickness of at least 100 Å (e.g., in a range of 600-1500 Å). In one or more embodiments, the metal comprises a plurality of layers each deposited at a different pressure (e.g., a first layer deposited on the substrate at the pressure in a range of 50-250 mTorr and a second layer deposited on the first layer at the pressure in a range of 2-50 mTorr).

The present disclosure further reports on how the deposition of a rough or pillar like structure in the metal film, reducing surface area contact to the substrate/surface in a highly controllable manner, aids in controlling adhesion when the deposition pressure is modulated. Thus, in one or more examples, the metal is at least one structured layer selected from a patterned layer, a roughened layer, a non-uniform layer, a layer including voids, and a layer comprising pillars.

In one example, PVD deposition with pressure modulation is used to fabricate a Backside Counter Electrode (BCE) for a glucose sensor, where the metal to glass substrate adhesion is strong enough to survive processing and laser cutting, but weak enough to allow easy physical removal from the glass substrate for assembly processes.

Also illustrated herein is a PVD process is used to fabricate and place an electrode on both the top-side and back-side of the sensor flex. Conventional methods only place the electrode on the top-side of the sensor flex. Thus, embodiments of the present invention obviate the need to have multiple sensor flexes in one device. In one example, the counter electrode is placed on the back-side of the flex and the work electrode remains on the top-side of the sensor flex. Example electrode surface metals for the counter electrode include, but are not limited to, gold, platinum, silver, etc. In one or more embodiments, the conventional electroplated platinum layer in the working electrode is replaced by a layer including platinum pillars, and the conventionally electroplated reference electrode is replaced by a reference electrode including silver-silver chloride that is screen printed or dispensed, etc.

More generally, applications of the adhesion control method described herein include fabrication of devices where adhesion is the key factor for specific processes, for example, during fabrication or processing of flexible circuit arrays, microelectromechanical (MEMS) devices, semiconductor devices, and biomedical electrodes (neural, cardiac, glucose, and lactate electrodes, etc).

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

As shown in FIG. 3, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

FIG. 7E shows Table 1 and FIG. 7F shows Table 2.

FIG. 8A illustrates the test sample without gold pillars and FIG. 8B illustrates the test sample with gold pillars, according to one or more embodiments of the present invention.

FIGS. 10A-10D illustrate the film on the test samples fabricated using various sputtering conditions and after laser cutting with an example electrode pattern, according to one or more embodiments of the present invention.

FIG. 15A illustrates the film on the test sample of FIG. 6A comprising a gold layer deposited using sputtering conditions including 100 mTorr pressure, 1.5 kW power, for a duration of 5 minutes, according to one or more embodiments of the present invention.

FIG. 15B illustrates the film on the test sample of FIG. 14 comprising a first gold layer deposited using sputtering conditions including 100 mTorr pressure, 1.5 kW power, for a duration of 5 minutes and the second gold layer deposited using sputtering conditions including 4 mTorr pressure, 0.2 kW power, for a duration of 10 minutes, according to one or more embodiments of the present invention.

FIGS. 15C, 15D, and 15E illustrate the film on the test sample of FIG. 14 with two gold layers and deposited using the conditions for FIG. 15B has an adhesion that varies depending on position on the surface area.

FIGS. 21A-21C illustrate SITS results for a control sensor (sensor 130 illustrated in FIG. 1F), wherein FIGS. 21A and 21B plot electrical current (ISIG) as a function of time (date in month of May) and FIG. 21C plots Vcounter as a function of time (date in month of May), and the different traces in FIGS. 21A-21C represent results for different sensors.

FIGS. 21D-21F illustrates SITS results for the sensor of FIG. 1G (representing performance of the sensor FIG. 1D), according to one or more embodiments of the present invention, wherein FIGS. 21D and 21E plot ISIG as a function of time (date in month of May) and FIG. 21F plots Vcounter (the voltage at the counter electrode) as a function of time (date in month of May). The different traces in FIGS. 21D-21F represent results for different sensors and show capability of the smooth backside CE design to support sensor function and importantly reduced sensor-to-sensor performance variability and improved performance stability over the lifetime of the tests, for the sensor of FIG. 1D as compared to the sensor of FIG. 1F.

FIG. 23 is a schematic illustrating a method of fabricating a sensor or sensor flex using the flowchart of FIG. 22 according to one or more embodiments of the present invention.

FIG. 24 is a flowchart illustrating a method of depositing films on a substrate, according to one or more embodiments of the present invention.

FIG. 25 is a flowchart illustrating a method of making a device on a substrate, according to one or more embodiments of the present invention.

DETAILED DESCRIPTION OF THE INVENTION

Figure 1A:
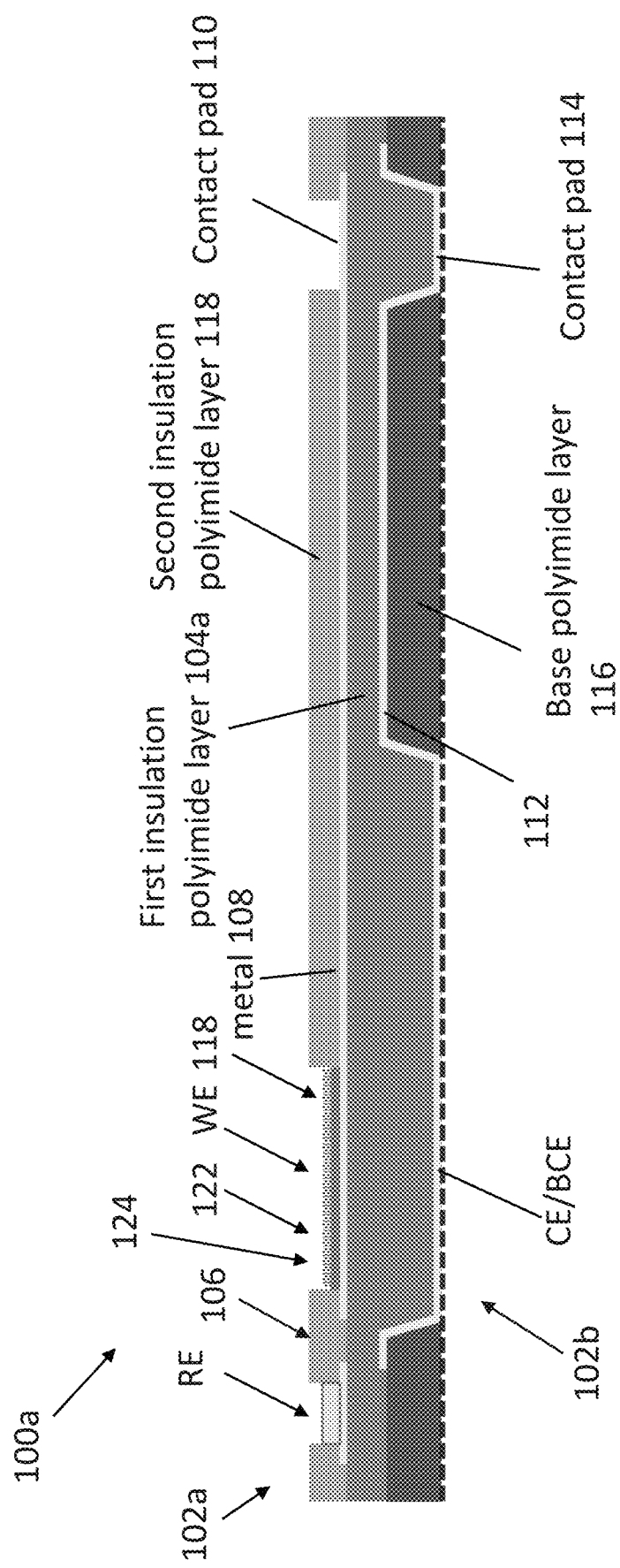
FIGS. 1A-1D illustrate amperometric sensors with WE and CE on opposite sides, according to one or more embodiments.

Unless otherwise defined, all terms of art, notations, and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All numbers recited in the specification and associated claims that refer to values that can be numerically characterized with a value other than a whole number (e.g. a thickness) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Furthermore, all publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors elements, including for example, those disclosed in U.S. Patent Application Nos. 20050115832, 20050008671, 20070227907, 20400025238, 20110319734, 20110152654 and Ser. No. 13/707,400 filed Dec. 6, 2012, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO 03/036310 WO 08/042, 625, and WO 03/074107, and European Patent Application EP 1153571, the contents of each of which are incorporated herein by reference.

A. Illustrative Embodiments of the Invention and Associated Characteristics

Controllable adhesion of Physical Vapor Deposited (PVD) metal films is a wide spread challenge and problem throughout the MEMS and semiconductor industries as well as for flex circuit applications. For a variety of applications, Metal films often need to maintain very specific levels of adhesion to surfaces/substrates they are deposited on. In some cases strong adhesion is required, while in other applications weak adhesion is required. In the most challenging cases, a mixture of weak and strong adhesion is required, where the adhesion force is strong enough to withstand specific aspects of an application but weak enough for other aspects of the application to function properly.

As illustrated herein, the present disclosure describes an efficient method to adjust and control the adhesion of PVD films deposited on surfaces/substrates. A comprehensive series of studies evaluating PVD deposition factors and their influence on adhesion property were performed and pressure was discovered to be a critically significant factor for adjusting adhesion. This single factor is a key component of PVD deposition and is controllable in the PVD process; as such, pressure is an ideal factor to utilize for controlling film adhesion. Illustrative methods described herein are applicable to all PVD systems utilized for depositing thin or thick films.

Of particular interest from a device perspective, controlling adhesion using pressure modulation enables fabrication and manufacturing of devices where PVD layers are deposited in direct contact with a carrier substrate and while being releasable based on an adhesion metric. FIG. 1A illustrates an example of such as a device useful in diabetes applications such as, but not limited to, continuous glucose monitoring (CGM) sensors where electrodes are on both sides (topside and backside) of a single sensor flex. As illustrated herein, the pressure modulation provides a highly efficient approach to adjust the adhesion of the backside electrode to the carrier substrate, enabling release at a specific point in the overall downstream manufacturing process. Placing the contact pads for each of the electrodes on either side of the sensor flex enables a wider array of connection schemes to the transmitter. Moreover, adjusting adhesion can be used to minimize the amount of newly-added processing steps for the backside electrode. As a whole, the adhesion control illustrated herein may be used to reduce manufacturing complexity, compared to conventional sensors, by significant margins.

Importantly, the novel methods of controlling adhesion described herein can be accomplished using standard materials, equipment and facilities associated with PVD.

The methods for forming analyte sensors that comprise the electrodes disclosed herein can include a number of steps. For example, such methods can include forming a working electrode, a counter electrode and a reference electrode on the base substrate and/or forming a plurality of contact pads on the base substrate, and/or forming a plurality of electrical conduits on the base substrate. In certain embodiments of the invention, the methods comprise forming a plurality of working electrodes, counter electrodes and reference electrodes clustered together in units consisting essentially of one working electrode, one counter electrode and one reference electrode. The electrodes are formed on the base substrate and these clustered units are longitudinally distributed on at least one longitudinal arm of the base substrate in a repeating pattern of units. Optionally in such methods, the working electrode is formed as an array of electrically conductive members disposed on the base substrate, the electrically conductive members are circular and have a diameter between 10 µm and 400 µm, and the array comprises at least 10 electrically conductive members. The methods can further comprise forming an analyte sensing layer on the working electrode, wherein the analyte sensing layer detectably alters the electrical current at the working electrode in the presence of an analyte. Typically these methods also include forming an analyte modulating layer on the analyte sensing layer, wherein the analyte modulating layer modulates the diffusion of analyte therethrough.

Yet another embodiment of the invention is an analyte sensor apparatus that includes a base substrate comprising a well that holds a metal electrode composition formed using the sputtering processes disclosed herein. In such embodiments, the structure of the platinum composition is formed to include a central planar region and an edge or ridge like region that surrounds the central planar region. In such embodiments, the thickness or height of the metal composition at the edge is less than 2× the average thickness of metal composition in the central planar region. In certain embodiments of the invention, the well comprises a lip that surrounds the well; and the edge region of the metal composition is below the lip of the well. Typically in these embodiments, both the central planar region forms an electroactive surface of a working electrode in the sensor. Sensor embodiments of the invention typically include additional layers of material coated over the working electrode, for example an analyte sensing layer disposed over the working electrode, one that detectably alters the electrical current at the working electrode in the presence of an analyte as well as an analyte modulating layer disposed over the analyte sensing layer that modulates the diffusion of analyte therethrough.

In typical embodiments of the invention, the electrode is formed in a well of a base substrate comprising a dielectric material (e.g. a polyimide). Typically, the well includes a conductive material disposed at the bottom of the well (e.g. Au). Optionally the well in the base substrate is rectangular or circular. In certain embodiments of the invention, the base substrate comprises at least 10, 20 or 30 wells formed into a microarray. In typical sensor embodiments, a base substrate is formed so that it includes a well that comprises a lip surrounding the well. In certain processes disclosed herein, the metal composition is sputtered so that the metal composition is below the lip of the well. In addition, a variety of different electrically conductive elements can be disposed on the base substrate. In some embodiments of the invention, the base substrate comprises a plurality of reference electrodes, a plurality of working electrodes and a plurality of counter electrodes clustered together in units consisting essentially of one working electrode, one counter electrode and one reference electrode, and the clustered units are longitudinally distributed on the base substrate in a repeating pattern of units.

Embodiments of the invention include further elements designed for use with the sensor apparatuses that are disclosed herein, for example those that are designed to analyze electrical signal data obtained from sputtered electrodes disposed on the base substrate. In some embodiments of the invention, the analyte sensor apparatus includes a processor and a computer-readable program code having instructions, which when executed, cause the processor to assess electrochemical signal data obtained from at least one working electrode and then compute analyte concentrations based upon the electrochemical signal data obtained from the working electrode. In certain embodiments of the invention, the processor compares electrochemical signal data obtained from multiple working electrodes in order to, for example, adapt different electrodes to sense different analytes, and/or to focus on different concentration ranges of a single analyte; and/or to identify or characterize spurious sensor signals (e.g. sensor noise, signals caused by interfering compounds and the like) so as to enhance the accuracy of the sensor readings.

In some embodiments of the invention, the base structure comprises a flexible yet rigid and flat structure suitable for use in photolithographic mask and etch processes. In this regard, the base structure typically includes at least one surface having a high degree of uniform flatness. Base structure materials can include, for example, metals such as stainless steel, aluminum and nickel titanium memory alloys (e.g. NITINOL) as well as polymeric/plastic materials such as delrin, etc. Base structure materials can be made from, or coated with, a dielectric material. In some embodiments, the base structure is non-rigid and can be a layer of film or insulation that is used as a substrate for patterning electrical elements (e.g. electrodes, traces and the like), for example plastics such as polyimides and the like. An initial step in the methods of the invention typically includes the formation of a base substrate of the sensor. Optionally, the planar sheet of material is formed and/or disposed on a support such as a glass or ceramic plate during sensor production. The base structure can be disposed on a support (e.g. a glass plate) by PVD. This can then be followed by a sequence of photolithographic and/or chemical mask and etch steps to form the electrically conductive components. In an illustrative form, the base substrate comprises a thin film sheet of insulative material, such as a polyimide substrate that is used to pattern electrical elements. The base substrate structure may comprise one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof.

The methods of the invention include forming an electrically conductive layer on the base substrate that function as one or more sensing elements. Typically these sensing elements include electrodes, electrical conduits (e.g. traces and the like), contact pads and the like that are formed by one of the variety of methods known in the art such as photolithography, etching and rinsing to define the geometry of the active electrodes. The electrodes can then be made from electrochemically active materials having defined architectures, for example by using sputtered Pt black for the working electrode. A sensor layer such as a analyte sensing enzyme layer can then be disposed on the sensing layer by electrochemical deposition or a method other than electrochemical deposition such as spin coating, followed by vapor crosslinking, for example with a dialdehyde (glutaraldehyde) or a carbodi-imide.

In an exemplary embodiment of the invention, the base substrate is initially coated with a thin film conductive layer by electrode deposition, surface sputtering, or other suitable patterning or other process step. In one embodiment this conductive layer may be provided as a plurality of thin film conductive layers, such as an initial chrome-based layer suitable for chemical adhesion to a polyimide base substrate followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base substrate. In an illustrative sensor construction designed for use as a subcutaneous glucose sensor, each sensor trace can include two or three parallel sensor elements corresponding with two or three separate electrodes such as a working electrode, a counter electrode and a reference electrode.

Embodiments of the invention include methods of adding a plurality of materials to the surface(s) of the sputtered electrode(s). One such embodiment of the invention is a method of making a sensor apparatus (e.g. a glucose sensor) for implantation within a mammal comprising the steps of: providing a base substrate; forming a conductive layer on the base substrate, wherein the conductive layer includes an electrode formed from a sputtering process that generates metallic columns of a certain architecture, forming an analyte sensing layer on the conductive layer, wherein the analyte sensing layer includes a composition that can alter the electrical current at the electrode in the conductive layer in the presence of an analyte (e.g. glucose oxidase); optionally forming a protein layer over the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer.

In the working embodiments of the invention that are disclosed herein, the analyte sensing layer comprises glucose oxidase. Optionally, the apparatus comprises an adhesion promoting layer disposed between the analyte sensing layer and the analyte modulating layer. In some embodiments of the invention, the analyte modulating layer comprises a hydrophilic comb-copolymer having a central chain and a plurality of side chains coupled to the central chain, wherein at least one side chain comprises a silicone moiety. Typically, the apparatus comprises a biocompadble material on an external surface that is adapted to contact biological tissues or fluids when implanted in vivo. In the working embodiments of the invention that are disclosed herein, the analyte sensor apparatus is an amperometric glucose sensor exhibits a highly desirable oxygen response profile. In such embodiments, the amperometric glucose sensor generates a first signal in a solution comprising 100 mg/dL glucose and 5% oxygen and a second signal in a solution comprising 100 mg/dL glucose and 0.1% oxygen (i.e. test conditions where the only substantive difference is the % oxygen), and the first signal and the second signal differ by less than 10%.

Additional functional coatings or cover layers can then be applied to an electrode or other senor element by any one of a wide variety of methods known in the art, such as spraying, dipping, etc. Some embodiments of the present invention include an analyte modulating layer deposited over an enzyme-containing layer that is disposed over a working electrode. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. Microfabrication of the underlying layers can be a factor which affects dimensional control over the analyte modulating membrane layer as well as the exact composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein.

In some embodiments of the invention, the sensor is made by methods which apply an analyte modulating layer that comprises a hydrophilic membrane coating which can regulate the amount of analyte that can contact the enzyme of the sensor layer. For example, a cover layer that is added to the glucose sensing elements of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention, the analyte modulating layer comprises a hydrophilic polymer. In some embodiments of the invention, the analyte modulating layer comprises a linear polyurethane/polyurea polymer and/or a branched acrylate polymer; and/or a mixture of such polymers.

In some embodiments of the methods of invention, an adhesion promoter layer is disposed between a cover layer (e.g. an analyte modulating membrane layer) and an analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art.

The finished sensors produced by such processes are typically quickly and easily removed from a support structure (if one is used), for example, by cutting along a line surrounding each sensor on the support structure and then peeling from the support structure. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. As illustrated herein, since the base substrate is sufficiently weakly adhered directly to the underlying support, the sensors can be lifted quickly and easily peeled from the support structure, without significant further processing steps or potential damage due to stresses incurred by excessive force being applied to peel the attached sensors from the support structure. The support structure can thereafter be cleaned and reused, or otherwise discarded. The functional coating layer(s) can be applied either before or after other sensor components are removed from the support structure (e.g. by cutting).

Embodiments of the invention also include methods of sensing an analyte (e.g. glucose) within the body of a mammal (e.g. a diabetic patient), the method comprising implanting a analyte sensor embodiment disclosed herein into an in vivo environment and then sensing one or more electrical fluctuations such as alteration in current at the working electrode and correlating the alteration in current with the presence of the analyte, so that the analyte is sensed. Typically, this method comprises implanting a glucose sensor disclosed herein within the interstitial space of a diabetic individual, sensing an alteration in current at the working electrode in the presence of glucose; and then correlating the alteration in current with the presence of the glucose, so that glucose is sensed. While typical embodiments of the invention pertain to glucose sensors, the sputtered sensor electrodes disclosed herein can be adapted for use with a wide variety of devices known in the art.

As discussed in detail below, embodiments of the invention include sensor systems comprising addition elements designed to facilitate sensing of an analyte. For example, in certain embodiments of the invention, the base material comprising the sensor electrodes is disposed within a housing (e.g. a lumen of a catheter) and/or associated with other components that facilitate analyte (e.g. glucose) sensing. One illustrative sensor system comprises a processor, a base comprising a first longitudinal member and a second longitudinal member, the first and second longitudinal members each comprising at least one electrode having an electrochemically reactive surface, wherein the electrochemically reactive surface generates an electrochemical signal that is assessed by the processor in the presence of an analyte; and a computer-readable program code having instructions, which when executed cause the processor to assess electrochemical signal data obtained from the electrodes; and compute an analyte presence or concentration based upon the electrochemical signal data obtained from the electrode. Embodiments of the invention described herein can also be adapted and implemented with amperometric sensor structures, for example those disclosed in U.S. Patent Application Publication Nos. 20070227907, 20400025238, 20110319734 and 20110152654, the contents of each of which are incorporated herein by reference.

B. Illustrative Analyte Sensor Constituents and Sensor Stacks Used in Embodiments of the Invention The following disclosure provides examples of typical elements/constituents used in sensor embodiments of the invention. While these elements can be described as discrete units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Figure 1B:
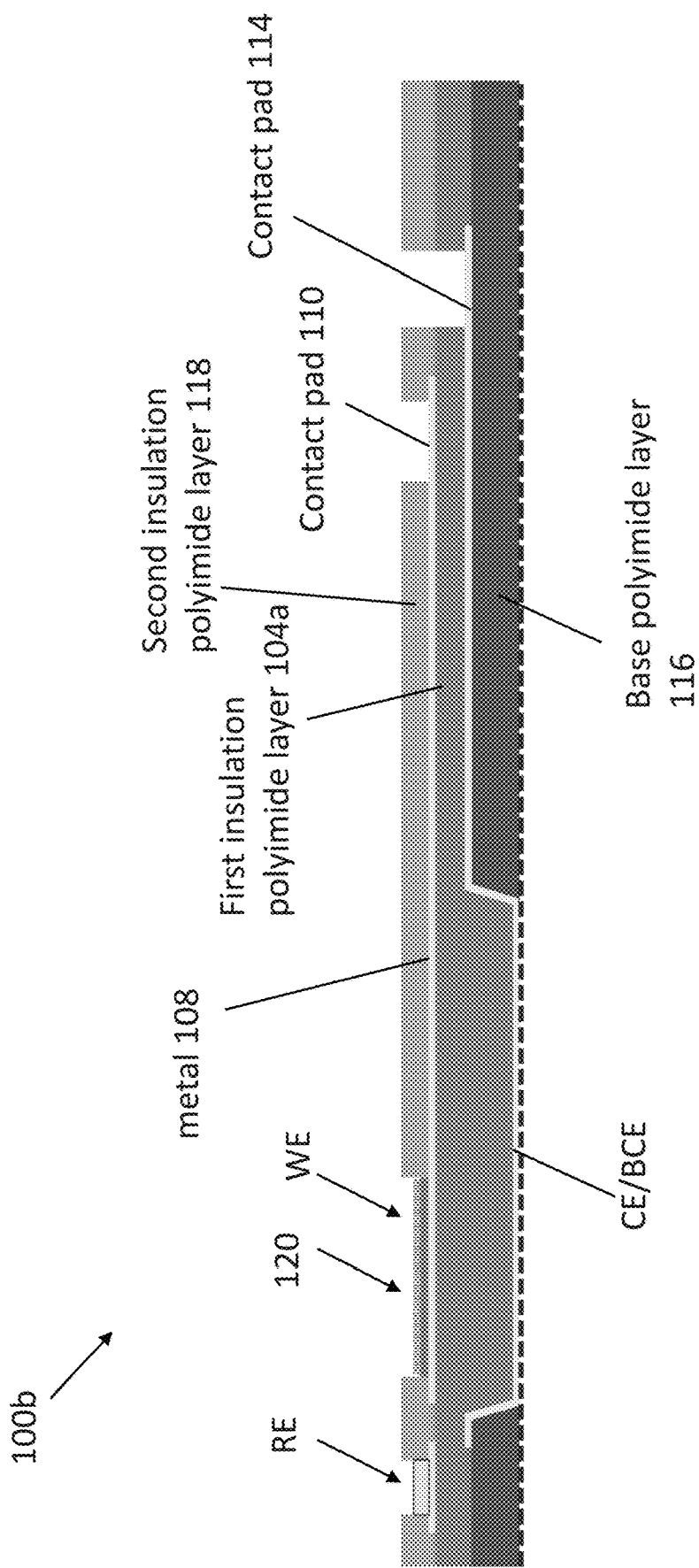
Figure 1C:
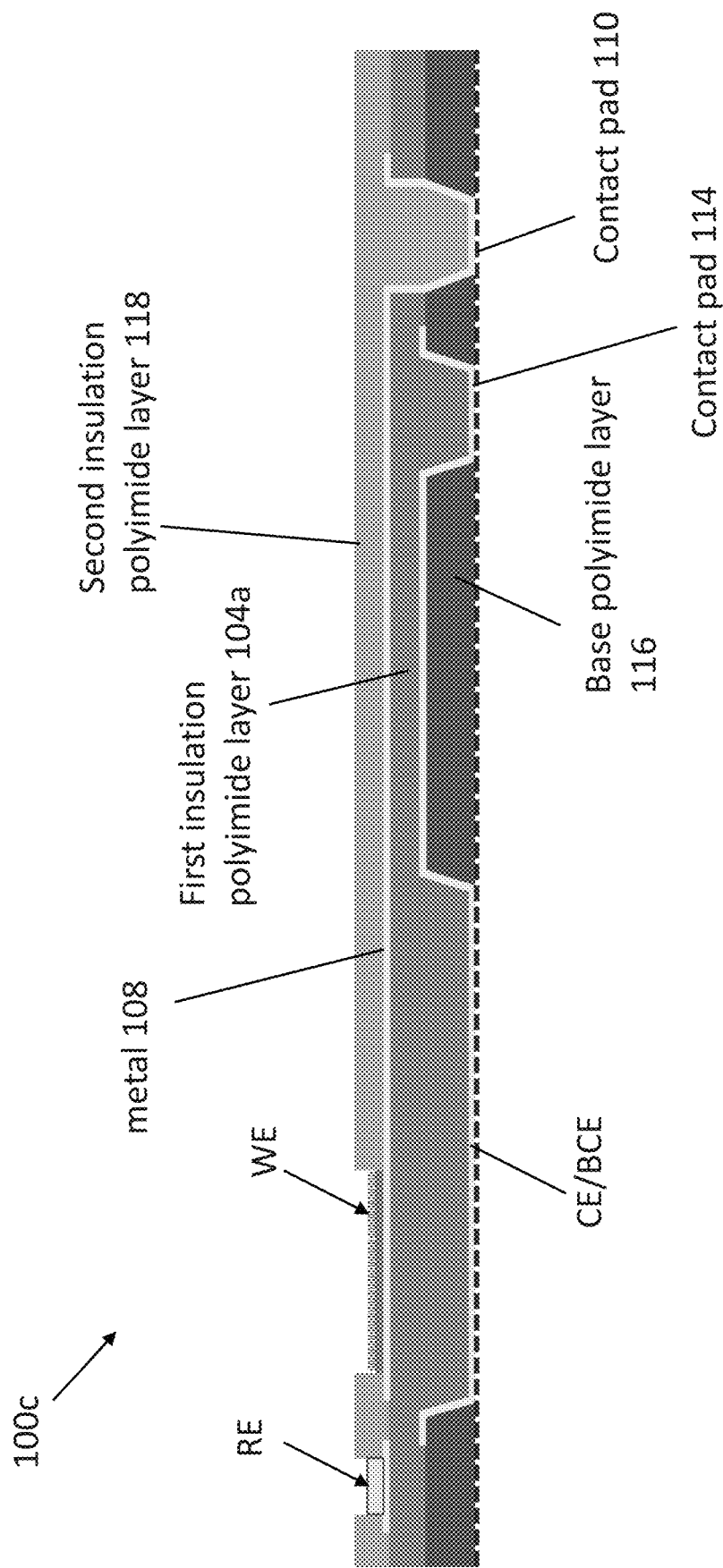

FIGS. 1A-1D illustrate embodiments of an analyte sensor apparatus 100a-100d comprising a working electrode (WE) on a first side 102a of an insulation layer 104a, 104b and a counter electrode (CE or BCE) on a second side 102b of the insulation layer 104a, 104b so that the insulation layer 104a, 104b is between the CE/BCE and the WE. FIGS. 1A-1D further illustrate a reference electrode (RE) on the first side 102a of the insulation layer 104a, 104b and insulation 106 between the RE and WE. Metal 108 deposited on the insulation layer 104a, 104b electrically contacts the WE and comprises a contact pad 110 for contacting the WE. Metal 112 or CE on the insulation layer 104a comprises the CE and contact pad 114 for contacting the CE. Also shown in FIGS. 1A-1C is a base layer 116 on the CE and second insulation layer 118 on the first insulation layer 104a, 104b and metal 108.

The WE comprises a metal composition 120 having an electroactive surface 122. In the examples illustrated in FIGS. 1A-1D, the WE comprises pillars 124 including the metal composition 120 and having the electroactive surface 122.

Figure 1D:
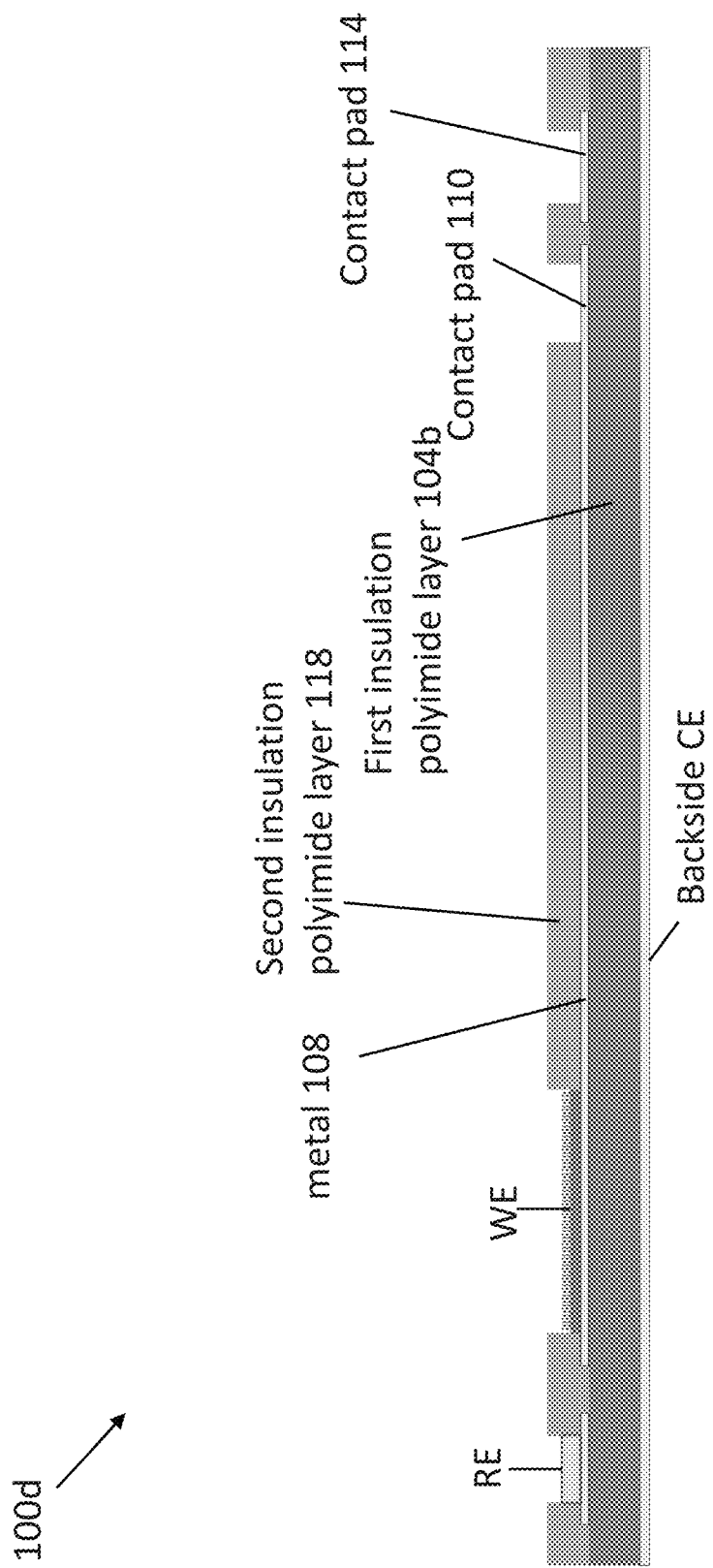

FIG. 1D illustrates a sensor 100d embodiment wherein the backside CE is/comprises a layer capable of controlling adhesion to a substrate as well as an electrode in the sensor apparatus 100d.

Figure 1E:
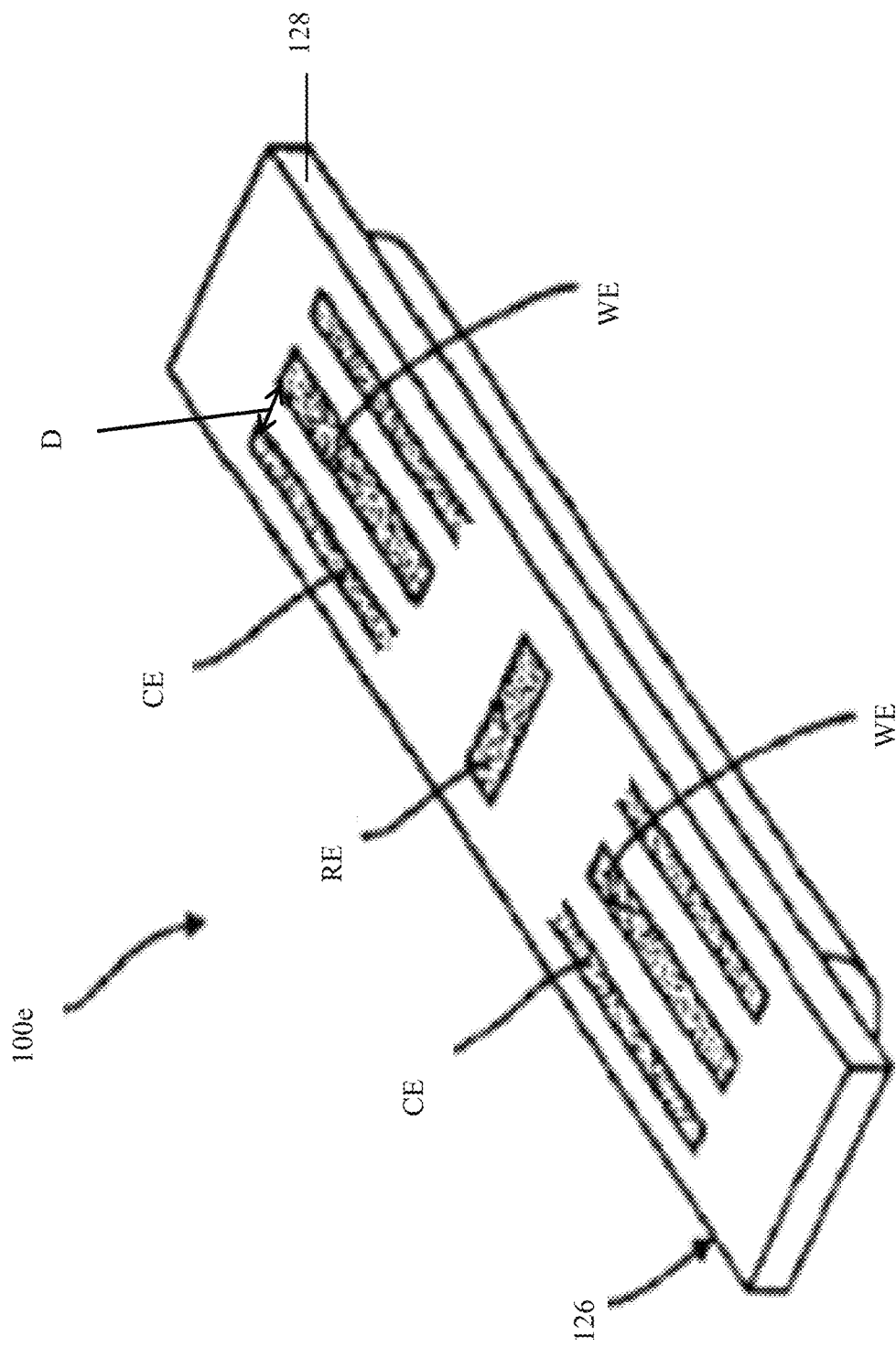
FIG. 1E illustrates an amperometric sensor with WE and CE on a same side of the device but separated by a distance D of at least 1 micrometer inches, according to one or more embodiments of the invention.

FIG. 1E illustrates an analyte sensor apparatus 100e, comprising a working electrode WE and a CE on a first side (same side) 126 of a substrate 128 and wherein the WE and the CE are spatially separated by a distance D of at least 1 micrometer inches, e.g., in a range of 1 micrometer-20 micrometers. The WE and the CE are non-interdigitated. The distance D is sufficiently large to reduce unwanted interactions between the WE and the CE (i.e., reducing the impact of the oxidation reaction at one electrode on the reduction reaction at the other electrode, and vice versa).

In one or more embodiments, the devices of FIG. 1A-1E are fabricated using PVD and/or electroplating.

Figures 1F, 1G:
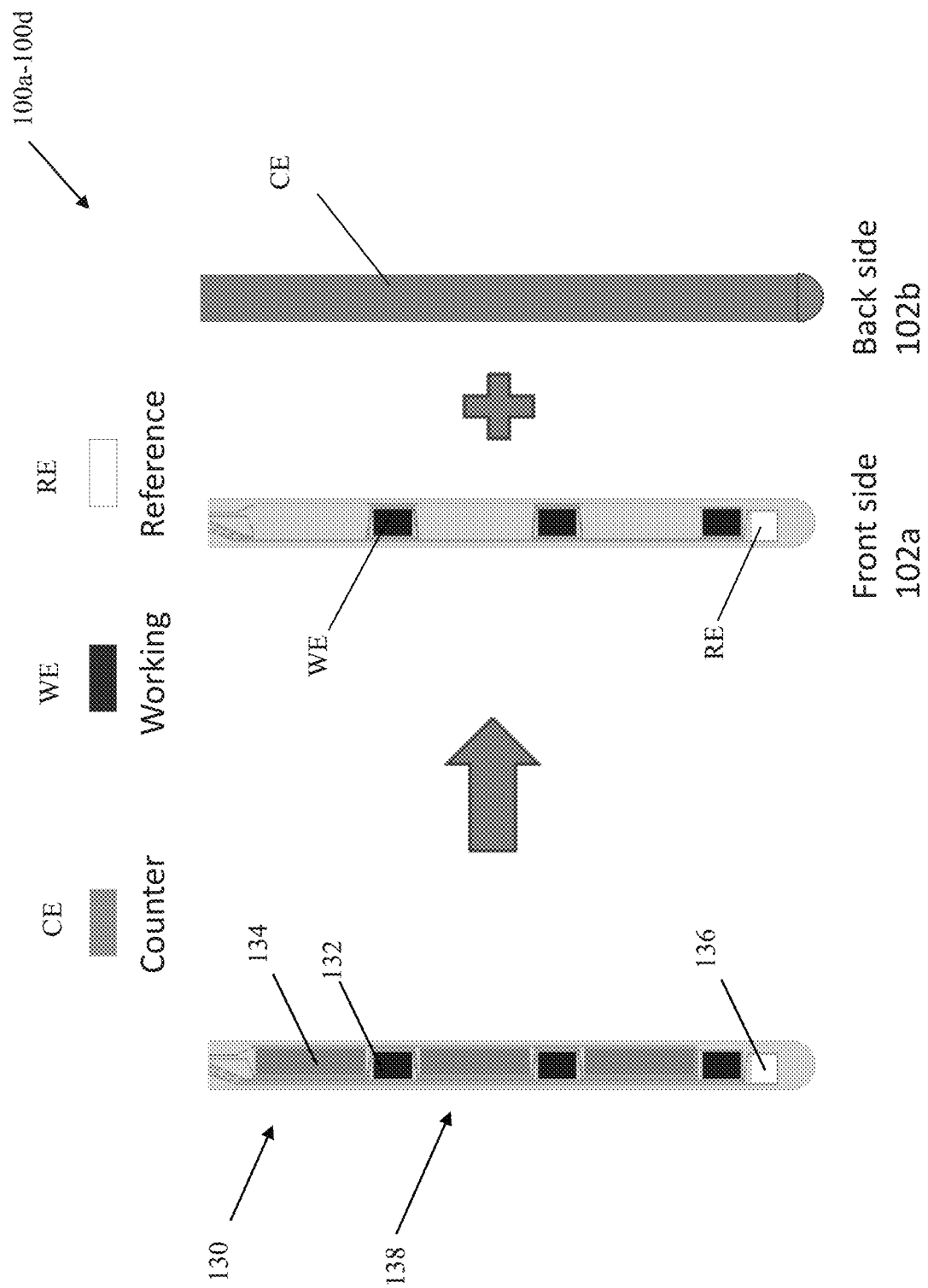
FIG. 1F and FIG. 1G compare structures of a control sensor (FIG. 1F) having an interdigitated working electrode and counter electrode, a reference electrode, and wherein the working electrode, counter electrode, and reference electrode are on one side only and are sufficiently close to exhibit undesirable electrode interactions, with sensors comprising electrodes on opposite sides (FIG. 1G) according to one or more embodiments of the present invention).

FIGS. 1F and 1G compare the structure of a control sensor 130 having an interdigitated working electrode 132 and counter electrode 134 and a reference electrode 136 on one side 126 of the device 130 with the sensor FIG. 1G representing embodiments 100a-100d comprising electrode WE on a first side 102a and electrode CE on a second side 102b. The working electrode 132 and control electrode 134 in the control device 130 also have a smaller separation that causes undesirable interactions between the electrodes 132 and 134.

Figure 1H:
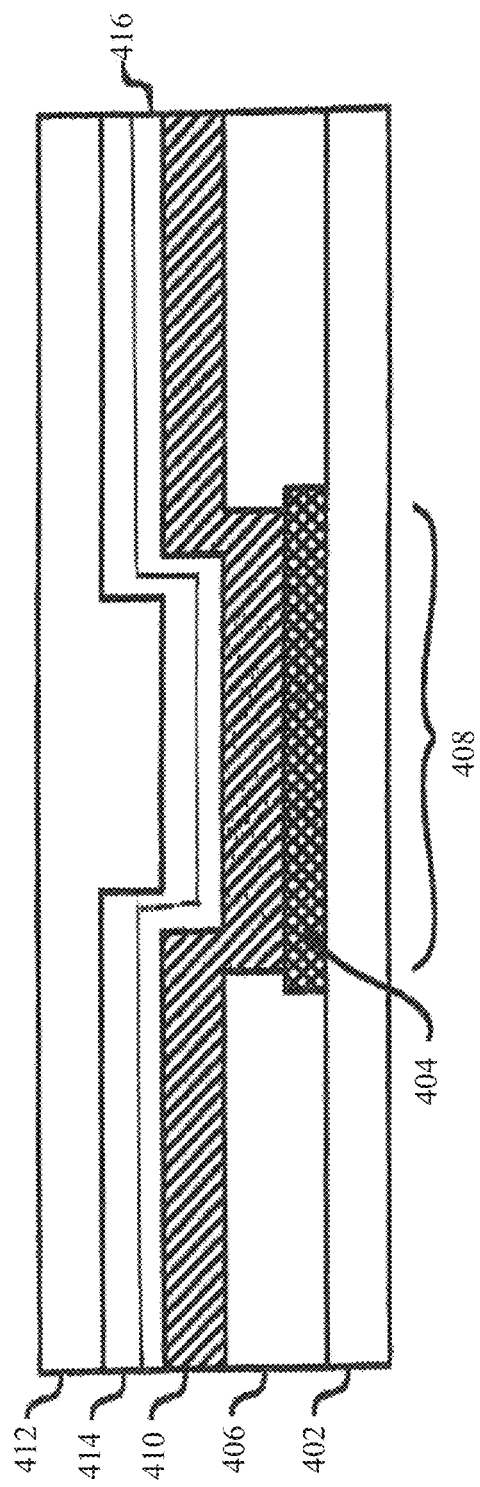
FIG. 1H illustrates the plurality of planar layered elements used in an amperometric sensor.

In one or more embodiments, the sensors 100a-e includes further layers/coatings/constitutents (e.g., on the WE) so as to enable operation as a glucose sensor (e.g., for diabetes applications), as illustrated in FIG. 1H. The further constituents include the following.

Base Constituent

Sensors of the invention typically include a base constituent (see, e.g. element 104b in FIG. 1D, element 402 in FIG. 1H, element 128 in FIG. 1E, or element 116 in FIGS. 1A-1D). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

Conductive Constituent

The electrochemical sensors of the invention typically include a conductive constituent disposed upon the base constituent that includes at least one electrode comprising a metal for contacting an analyte or its byproduct (e.g. oxygen and/or hydrogen peroxide) to be assayed (see, e.g. WE in FIGS. 1B-1F). The term "conductive constituent" is used herein according to art accepted terminology and refers to electrically conductive sensor elements such as electrodes, contact pads, traces and the like. An illustrative example of this is a conductive constituent that forms a working electrode that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 410 or a reaction product of this interaction (e.g. hydrogen peroxide). Illustrative examples of such elements include electrodes which are capable of producing variable detectable signals in the presence of variable concentrations of molecules such as hydrogen peroxide or oxygen.

In addition to the working electrode, the analyte sensors of the invention typically include a reference electrode (RE) or a combined reference and counter electrode (also termed a quasi-reference electrode or a counter/reference electrode). If the sensor does not have a counter/reference electrode then it may include a separate counter electrode (CE), which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure. In certain embodiments of the invention, the reactive surfaces of the electrodes are of different relative areas/sizes, for example a 1× reference electrode, a 3.2× working electrode and a 6.3× counter electrode.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant applied potential. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly(ethylene glycol), polyethersulfones, polytetra-fluoroethylenes, the perfluoronated ionomer Nafion™, polyphenylenediamine, epoxy and the like.

Analyte Sensing Constituent

The electrochemical sensors of the invention include an analyte sensing constituent disposed on the the electrodes of the sensor (see, e.g. element 410 in FIG. 1H). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard, the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde. Other suitable cross-linkers also may be used, as will be evident to those skilled in the art.

As noted above, in some embodiments of the invention, the analyte sensing constituent includes an agent (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

Protein Constituent

The electrochemical sensors of the invention optionally include a protein constituent disposed between the analyte sensing constituent and the analyte modulating constituent (see, e.g. element 416 in FIG. 1H). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 414 in FIG. 1H). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as 3-aminopropyltrimethoxysilane.

Analyte Modulating Constituent

The electrochemical sensors of the invention include an analyte modulating constituent disposed on the sensor (see, e.g. element 412 in FIG. 1H). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally, such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The analyte modulating sensor membrane assembly serves several functions, including selectively allowing the passage of glucose therethrough (see, e.g. U.S. Patent Application No. 2011-0152654).

Cover Constituent

The electrochemical sensors of the invention include one or more cover constituents, which are typically electrically insulating protective constituents (see, e.g. element 406 in FIG. 1H). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

FIG. 1H illustrates a cross-section of a typical sensor embodiment 400 of the present invention that includes constituents discussed above. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 1H. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 1H includes a base substrate layer 402 to support the sensor 400. The base substrate layer 402 can be made of a material such as a metal and/or a ceramic and/or a polymeric substrate, which may be self-supporting or further supported by another material as is known in the art. Embodiments of the invention include a conductive layer 404 which is disposed on and/or combined with the base substrate layer 402. Typically, the conductive layer 404 comprises one or more electrically conductive elements that function as electrodes. An operating sensor 400 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 402 and/or conductive layer 404 can be generated using many known techniques and materials. In certain embodiments of the invention, the electrical circuit of the sensor is defined by etching the disposed conductive layer 404 into a desired pattern of conductive paths. A typical electrical circuit for the sensor 400 comprises two or more adjacent conductive paths with regions at a proximal end to form contact pads and regions at a distal end to form sensor electrodes. An electrically insulating cover layer 406 such as a polymer coating can be disposed on portions of the sensor 400. Acceptable polymer coatings for use as the insulating protective cover layer 406 can include, but are not limited to, non-toxic biocompatible polymers such as silicone compounds, polyimides, biocompatible solder masks, epoxy acrylate copolymers, or the like. In the sensors of the present invention, one or more exposed regions or apertures 408 can be made through the cover layer 406 to open the conductive layer 404 to the external environment and to, for example, allow an analyte such as glucose to permeate the layers of the sensor and be sensed by the sensing elements. Apertures 408 can be formed by a number of techniques, including laser ablation, tape masking, chemical milling or etching or photolithographic development or the like. In certain embodiments of the invention, during manufacture, a secondary photoresist can also be applied to the protective layer 406 to define the regions of the protective layer to be removed to form the aperture(s) 408. The exposed electrodes and/or contact pads can also undergo secondary processing (e.g. through the apertures 408), such as additional plating processing, to prepare the surfaces and/or strengthen the conductive regions.

In the sensor configuration shown in FIG. 1H, an analyte sensing layer 410 is disposed on one or more of the exposed electrodes of the conductive layer 404. Typically, the analyte sensing layer 410 is an enzyme layer. Most typically, the analyte sensing layer 410 comprises an enzyme capable of producing and/or utilizing oxygen and/or hydrogen peroxide, for example the enzyme glucose oxidase. Optionally, the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 410 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can be monitored by any one of a variety of sensor detector apparatuses such as a universal sensor amperometric biosensor detector or one of the variety of similar devices known in the art such as glucose monitoring devices produced by Medtronic Diabetes.

In embodiments of the invention, the analyte sensing layer 410 can be applied over portions of the conductive layer or over the entire region of the conductive layer. Typically the analyte sensing layer 410 is disposed on the working electrode which can be the anode or the cathode. Optionally, the analyte sensing layer 410 is also disposed on a counter and/or reference electrode. Methods for generating a thin analyte sensing layer 410 include brushing the layer onto a substrate (e.g. the reactive surface of a platinum black electrode), as well as spin coating processes, dip and dry processes, low shear spraying processes, ink-jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by a sputtering process).

Typically, the analyte sensing layer 410 is coated and or disposed next to one or more additional layers. Optionally, the one or more additional layers includes a protein layer 416 disposed upon the analyte sensing layer 410. Typically, the protein layer 416 comprises a protein such as human serum albumin, bovine serum albumin or the like. Typically, the protein layer 416 comprises human serum albumin. In some embodiments of the invention, an additional layer includes an analyte modulating layer 412 that is disposed above the analyte sensing layer 410 to regulate analyte contact with the analyte sensing layer 410. For example, the analyte modulating membrane layer 412 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

Figure 3:
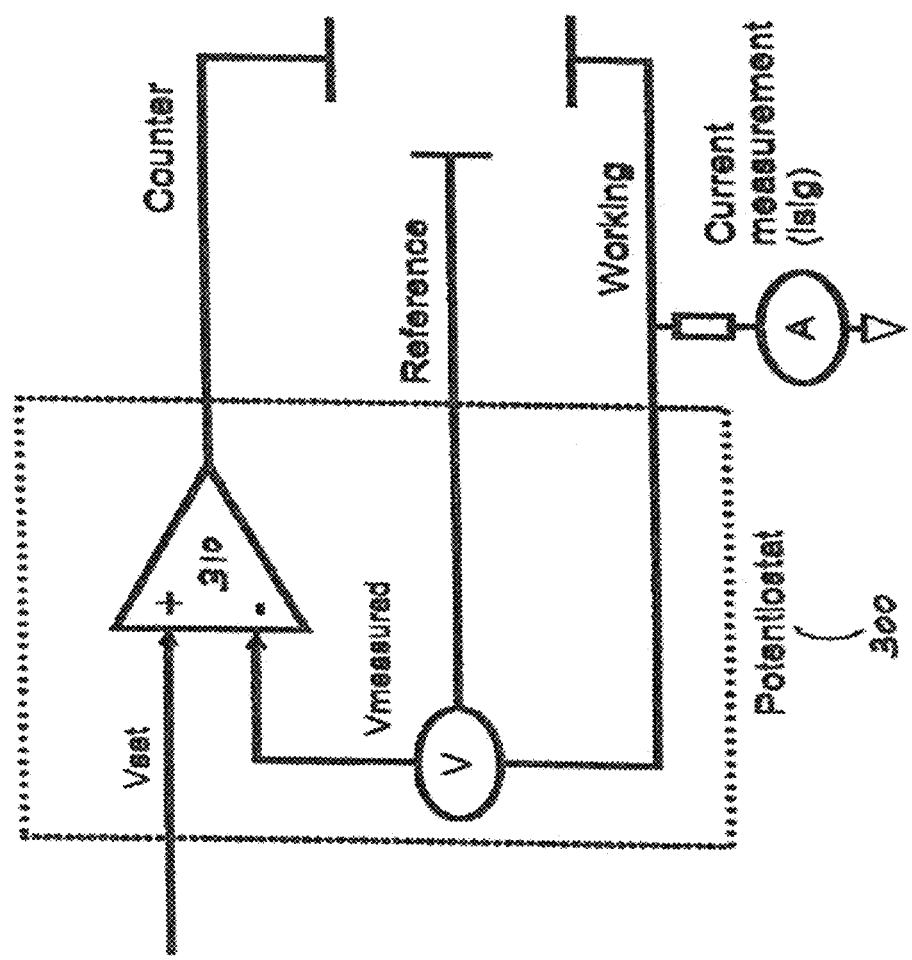
FIG. 3 shows a schematic of a potentiostat that may be used to measure current in embodiments of the present invention.

In certain embodiments of the invention, an adhesion promoter layer 414 is disposed between the analyte modulating layer 412 and the analyte sensing layer 410 as shown in FIG. 1H in order to facilitate their contact and/or adhesion. In a specific embodiment of the invention, an adhesion promoter layer 414 is disposed between the analyte modulating layer 412 and the protein layer 416 as shown in FIG. 3 in order to facilitate their contact and/or adhesion. The adhesion promoter layer 414 can be made from any one of a wide variety of materials known in the art to facilitate the bonding between such layers. Typically, the adhesion promoter layer 414 comprises a silane compound. In alternative embodiments, protein or like molecules in the analyte sensing layer 410 can be sufficiently crosslinked or otherwise prepared to allow the analyte modulating membrane layer 412 to be disposed in direct contact with the analyte sensing layer 410 in the absence of an adhesion promoter layer 414.

C. Typical System Embodiments of the Invention

A specific illustrative system embodiment consists of a glucose sensor comprising a sputtered/PVD electrode composition as disclosed herein, a transmitter and receiver and a glucose meter. In this system, radio signals from the transmitter can be sent to the pump receiver at regular time periods (e.g. every 5 minutes) to provide real-time sensor glucose (SG) values. Values/graphs can be displayed on a monitor of the pump receiver so that a user can self monitor blood glucose and deliver insulin using their own insulin pump. Typically the sensor systems disclosed herein can communicate with other medical devices/systems via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values include a plurality of measurements of blood glucose.

Figure 2:
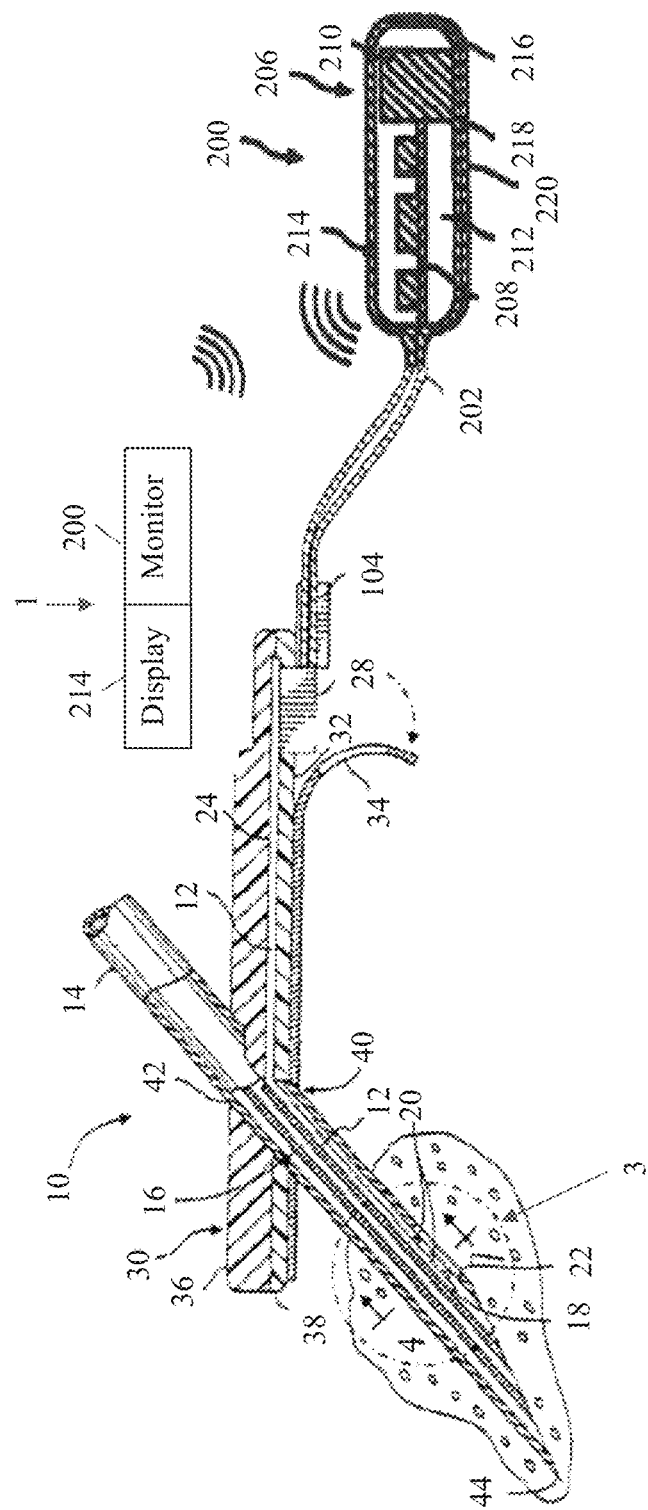
FIG. 2 provides a perspective view illustrating one type of subcutaneous sensor insertion set, a telemetered characteristic monitor transmitter device, and a data receiving device, elements that can be adapted for use with embodiments of the invention.

FIG. 2 provides a perspective view of one generalized embodiment of subcutaneous sensor insertion system that can be adapted for use with the sensor electrodes disclosed herein and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 2 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The base is designed so that the sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 200 by a connector block 28 (or the like) as shown and described in U.S. Pat. No. 5,482,473, entitled FLEX CIRCUIT CONNECTOR, which is incorporated by reference.

As shown in FIG. 2, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 200 is coupled to a sensor set 10 by a cable 402 through a connector 24 that is electrically coupled to the connector block 28 of the connector portion 24 of the sensor set 10.

In the embodiment shown in FIG. 2, the telemetered characteristic monitor 400 includes a housing 206 that supports a printed circuit board 208, batteries 210, antenna 212, and the cable 202 with the connector 204. In some embodiments, the housing 206 is formed from an upper case 214 and a lower case 216 that are sealed with an ultrasonic weld to form a waterproof (or resistant) seal to permit cleaning by immersion (or swabbing) with water, cleaners, alcohol or the like. In some embodiments, the upper and lower case 214 and 216 are formed from a medical grade plastic. However, in alternative embodiments, the upper case 214 and lower case 216 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 216 may have an underside surface coated with a suitable pressure sensitive adhesive layer 218, with a peel-off paper strip 220 normally provided to cover and protect the adhesive layer 118, until the sensor set telemetered characteristic monitor transmitter 200 is ready for use.

In the illustrative embodiment shown in FIG. 2, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. Nos. 4,562,751; 4,678,408; 4,685,903 or 4,573,994, to control delivery of insulin to a diabetic patient.

In the illustrative embodiment shown in FIG. 2, the sensor electrodes 10 may be used in a variety of sensing applications and may be configured in a variety of positions on a base structure and further be formed to include materials that allow a wide variety of functions. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 2, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 402 through a connector that is electrically coupled to the connector block 28 of the connection portion 24. In an alternative embodiment, the cable may be omitted. In this embodiment of the invention, the monitor 200 may include an appropriate connector for direct connection to the connection portion 24 of the sensor set 10. The sensor set 10 may be modified to have the connector portion 24 positioned at a different location, e.g., on top of the sensor set to facilitate placement of the monitor 200 over the sensor set.

As noted above, embodiments of the sensor elements and sensors can be operatively coupled to a variety of other system elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

FIG. 3 shows a schematic of a potentiostat that may be used to measure current in embodiments of the present invention. As shown in FIG. 3, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (Isig) that is output from the potentiostat.

Embodiments of the invention include devices which process display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide real-time sensor glucose (SG) values. Values/graphs are displayed on a monitor of the pump receiver so that a user can self monitor blood glucose and deliver insulin using their own insulin pump. Typically, an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values include a plurality of measurements of blood glucose.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

EXAMPLES

Common acronyms used in the examples include: WE Working Electrode; GOx Glucose Oxidase; HSA Human Serum Albumin; SITS Sensor In-vitro Test System; GLM Glucose Limiting Membrane (an embodiment of an analyte modulating layer); OQ Operational Qualification; SAR Surface Area Ratio; BTS Bicarbonate Test System; and EIS Electrochemical Impedance Spectroscopy. The BTS and SITS tests discussed in the example are tests used to evaluate aspects of sensor performance. SITS measures sensor signal in glucose solutions over 5-7 days, as wells as sensor oxygen response, temperature response, background current, linearity, stability, acetaminophen interference and response time. Dog tests are used to evaluate glucose sensor performance in vivo (Isig and calculated blood glucose level) in diabetic and non-diabetic dogs for up to 3 days and compares glucose level measured by continuous glucose sensors to that measured by a glucose meter.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The descriptions and specific examples, while indicating some embodiments of the present invention are given by way of illustration and not limitation. Many changes and modifications within the scope of the present invention may be made without departing from the spirit thereof, and the invention includes all such modifications.

Example 1: Sputtering Apparatus

Figure 4:
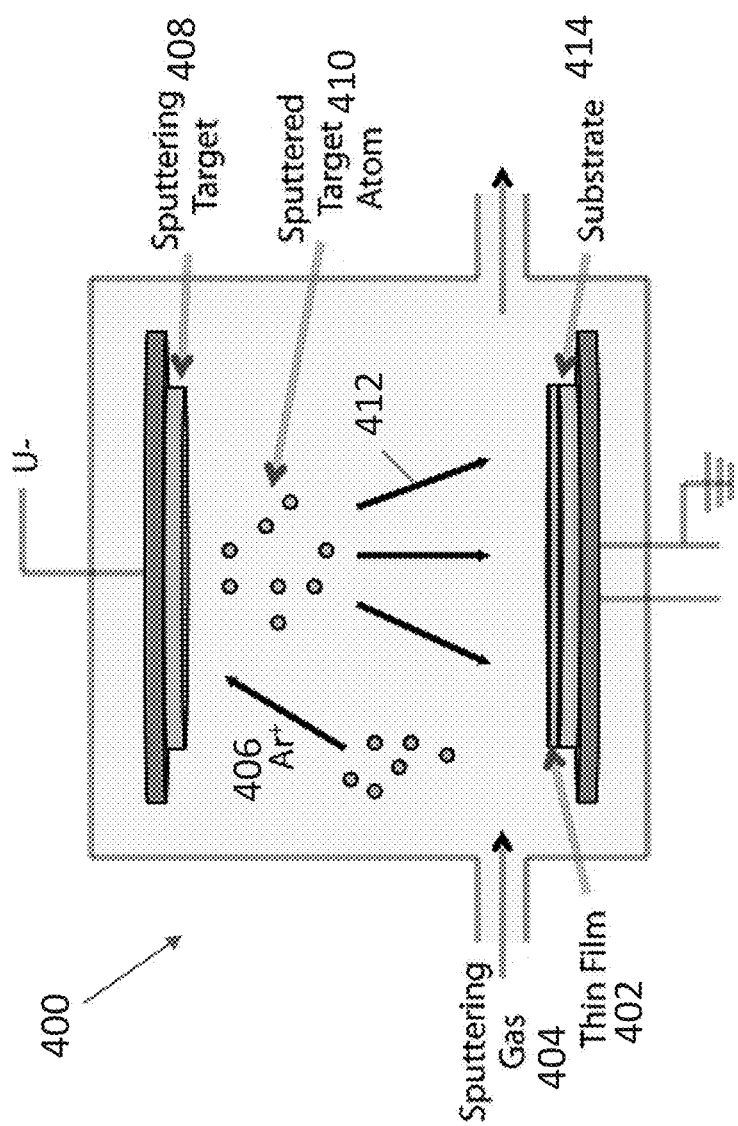
FIG. 4 illustrates an apparatus for depositing material using sputtering, according to one or more embodiments of the present invention.

FIG. 4 illustrates an apparatus comprising a chamber 400 for depositing material (e.g., a thin film 402) using sputtering. A sputtering gas 404 in the chamber 400 is ionized to form a plasma comprising ionized gas particles 406 (e.g., $Ar^+$). The ionized particles 406 bombard the sputtering target 408 comprising a metal composition. Collision of the ionized particles 406 with the sputtering target 408 knocks off material 410 (e.g., sputtered target atom) comprising the metal composition and accelerates 412 the material 410 to the target surface on the substrate 414, thereby forming a film 402 on the substrate 414. The ionized gas particles 406 are accelerated towards target using electric and/or magnetic fields applied by electrodes biased with voltage $U^-$. The particle collision is controlled by process power (i.e., power of the electric and/or magnetic fields until arrival of the ionized gas particles on the sputtering gas) and pressure and composition of the sputtering gas (or ionized gas particle composition and pressure).

Example 2: Sputtering Conditions for Controlling Adhesion

The following deposition conditions may impact adhesion.

High pressure deposition conditions may cause the deposited film to form under stress, leading to poor adhesion.

Deposition power may impact adhesion since higher deposition rates may induce void pockets, leading to poor adhesion.

High temperatures used during deposition may evaporate any remaining adsorbed water from the surfaces, improving adhesion.

Thicker films can generate stresses and worsen the adhesion.

Geometric area may also impact adhesion, and may be controlled by the formation of pillars at the interface between the film and the substrate.

In the experiments described herein, sputtering parameters including pressure, power, temperature, and thickness, and combinations of these parameters, were adjusted to determine their impact on adhesion and to determine the parameters/parameter values that achieve optimal adhesion for electrode processing. In one or more embodiments, the target for adhesion (or optimal adhesion) is strong enough to maintain adhesion of the base polyimide to the substrate during laser cutting, but weak enough to allow the base polyimide to be removed from the substrate for sensor assembly.

Figure 5:
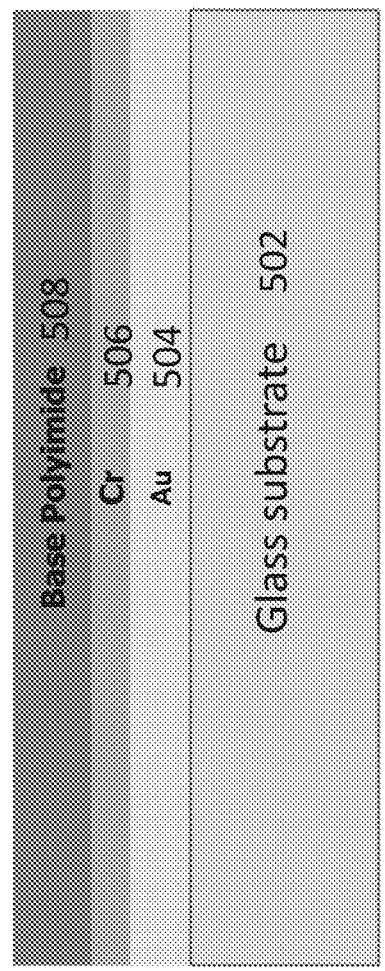
FIG. 5 illustrates a test sample comprising a layer stack on a glass substrate, according to one or more embodiments of the present invention.

FIG. 5 illustrates a test sample comprising a layer stack 500 on a glass substrate 502. The layer stack includes a gold (Au) layer 504 on the glass substrate, a chromium (Cr) layer 506 on the Au layer 504, and base polyimide layer 508 on the Cr layer 506.

Figure 6A:
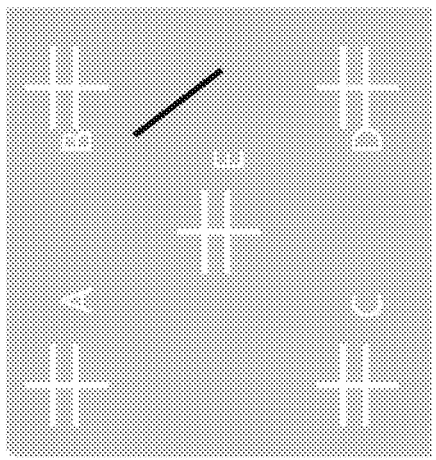
FIG. 6A illustrates different patterns A-E of knife scratches or laser cutting marks applied to the layer stack on the glass substrate that simulate the types of marks and cuts that may be applied during processing of an electrode in a glucose sensor according to one or more embodiments of the present invention.

FIG. 6A illustrates different patterns A-E of knife scratches or laser cutting marks applied to the layer stack 500 on the glass substrate 502 that simulate the types of marks and cuts that may be applied during processing of an electrode in a glucose sensor or other device.

Figure 6B:
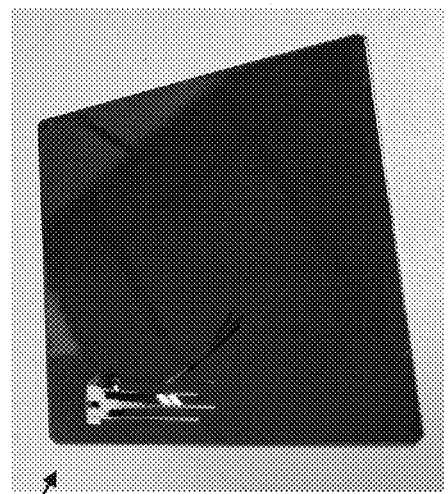
FIG. 6B illustrates the patterns applied to a silver layer on a glass substrate, showing that adhesion of the silver to the glass is too weak to allow reproduction of the markings on the silver layer.

FIG. 6B illustrates the patterns 600 applied to a silver layer on a glass substrate, showing that adhesion of the silver to the glass is too weak to allow reproduction of the markings on the silver layer.

Using the patterns of markings illustrated in FIG. 6A, a feasibility-efficiency-compatibility study was performed to discover the impact of metal (e.g., gold) sputtering conditions on the metal/glass (e.g., metal/glass) adhesion in the layer structure of FIG. 5.

Figure 7D:
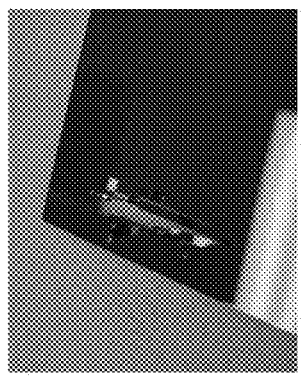
FIGS. 7A-7D illustrate different adhesion scores assigned to samples fabricated under different sputtering conditions according to one or more embodiments of the present invention.
Figure 7C:
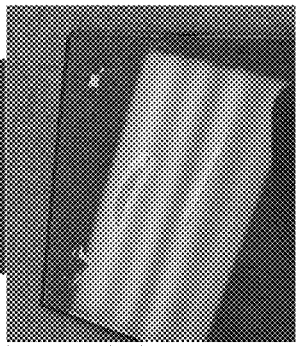
Figure 7B:
Figure 7A:
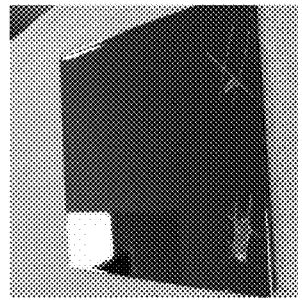

FIGS. 7A-7D illustrate how adhesion scores are assigned. FIG. 7A illustrates a score of 0 is assigned when the patterns of FIG. 6A can be accurately applied to the layer stack with highest quality and resolution of reproduction (representing the strongest adhesion of the layer stack to the glass substrate). As the scores increase, the adhesion decreases and the patterns of markings are less well reproduced in the layer stack (FIGS. 7B and 7C). FIG. 7D illustrates a score of 10 is assigned when the patterns of FIG. 6A cannot be accurately applied to, and reproduced in, the layer stack 500 (representing the weakest adhesion of the layer stack to the glass substrate). This adhesion score method is significantly less time consuming than performing a more quantitative analysis.

a. Experiment 1

The test samples of FIG. 6A were fabricated using the sputtering conditions of Table 1. The marking patterns of FIG. 6B were subsequently scratched/laser cut into each of the films on the test samples and an adhesion score was assigned to each reproduction, as shown in Table 1.

FIGS. 7A-7D show the test results. The sputtered structure in FIG. 7D was fabricated using sputtering conditions including 100 mT pressure, 1.6 kW power, a gold layer thickness of 897 Angstroms, and without heating.

The results show that the sputtering conditions for the samples 1-6 (highlighted in Table 1) had the strongest adhesion (adhesion score 0) allowing accurate reproduction of the markings of FIG. 6B. FIGS. 7A-7D and Table 1 in FIG. 7E shows the surprising and unexpected result that low pressure achieves extremely high adhesion and high pressure achieves low adhesion.

b. Experiment 2

Figure 9:
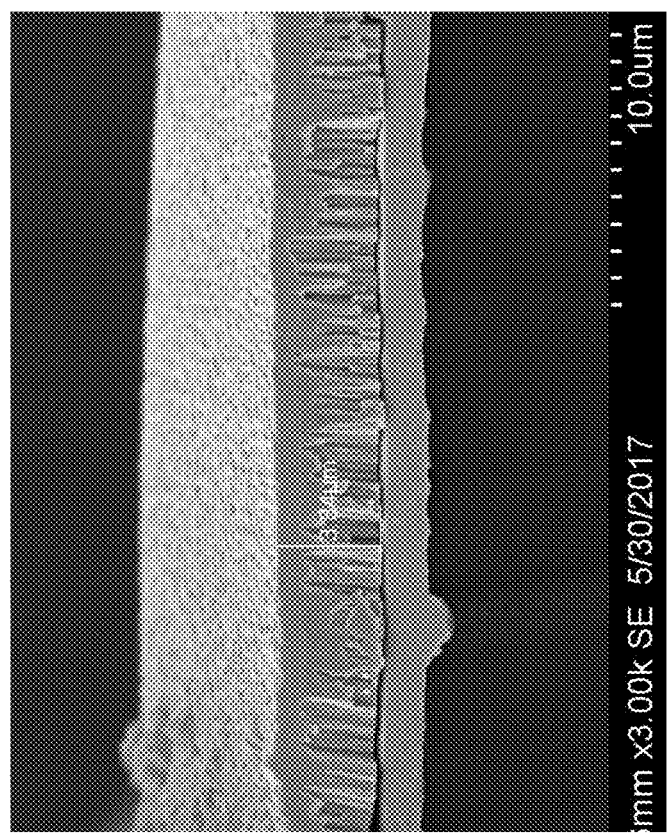
FIG. 9 is a scanning electron microscope (SEM) image of the pillared interface between the glass substrate and the gold layer, according to one or more embodiments of the present invention.

FIG. 8B illustrates a test sample 1000 comprising an Au layer 1002 including pillars 1004 at the interface between the Au layer 1002 and the glass substrate 1006. Different test samples 1000 were fabricated with the Au layer 1002 deposited under different sputtering conditions (as shown in Table 2). FIG. 9 is a scanning electron microscope image of the pillared interface between the glass substrate 1006 and the gold layer 1002.

The marking patterns of FIG. 6B were subsequently scratched/laser cut into each of the Au films 1002 in the test samples 1000 using a knife and an adhesion score was assigned to each reproduction, as shown in Table 2 in FIG. 7F.

FIG. 5 illustrates fabrication of a backside counter electrode comprising deposition of gold (Au) layer on a glass substrate, deposition of chromium (Cr) layer on the gold layer, deposition of polyimide including a base polyimide on the Cr layer, formation of openings in the polyimide, deposition of a Cr/Au stack inside the openings, and peeling off the base polyimide together with the Au layer and Cr layer from the glass substrate.

It is to be understood that this invention is not limited to the particular embodiments described, as such may, of course, vary. It is also to be understood that the terminology used The highlighted samples in Table 2 (samples 1-5 and 10) show low pressure sputtering achieves strong adhesion (low adhesion score). On the other hand, the results for samples 6-9 show that sputtering at high pressure (above 55 mTorr, e.g., 100 mTorr) achieves weak adhesion. A hypothesis is that the gold pillars decrease the contact area of gold/glass and increase the impact of pressure on adhesion. The results also show a thicker film has weaker adhesion to the glass substrate.

FIGS. 10A-10D illustrate the film of FIG. 6A including the gold pillars 1004, fabricated using various sputtering conditions, after laser cutting with an example electrode pattern. FIGS. 12A and 12B illustrate the pattern is well reproduced in the film fabricated using 100 mTorr pressure, 0.4 W power, and a 952 Å thick gold layer (FIG. 10A) and in the film fabricated using 100 mTorr pressure, 1.6 W power, and a 897 Å thick gold layer (FIG. 10B). FIGS. 10C and 10D illustrate the pattern is not well reproduced in the film fabricated using 100 mTorr pressure, 0.4 W power, and a 8922 Å thick gold layer (FIG. 10C) and in the film fabricated using 100 mTorr pressure, 1.6 W power, and a 10806 Å thick gold layer (FIG. 10B). These results show that when high pressure is used, adhesion can be increased using a relatively thinner gold layer (adhesion decreases as gold layer thickness increases).

Figure 11:
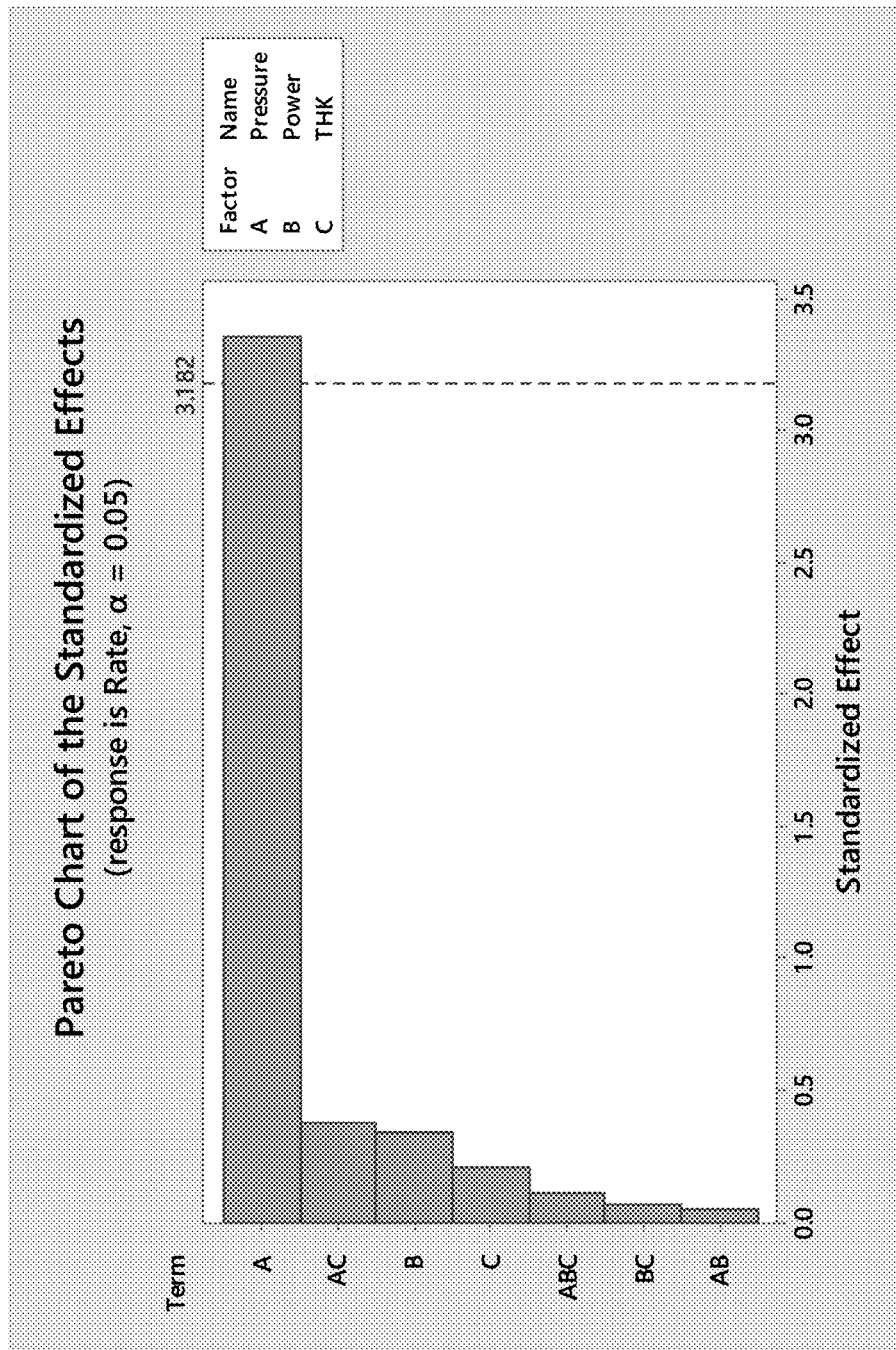
FIG. 11 illustrates a Pareto chart of the standardized effects of changing pressure, power, and gold thickness on adhesion for the samples fabricated using gold pillars at the interface between the gold layer and the glass substrate, according to one or more embodiments of the present invention.

FIG. 11 illustrates a Pareto chart of the standardized effects of changing different factors (pressure, power, and gold thickness) on adhesion for the samples 500 fabricated using gold pillars 1004 at the interface between the gold layer 504 and the glass substrate 502. In the Pareto chart, response is the rate of changing pressure, sputtering power, and gold layer thickness, and $\alpha=0.05$ is a parameter used to determine the statistically significant factors that control adhesion (in one or more examples, factors having a standardized effect on adhesion greater than $\alpha-0.05$ are considered statistically significant factors controlling adhesion).

Figure 12:
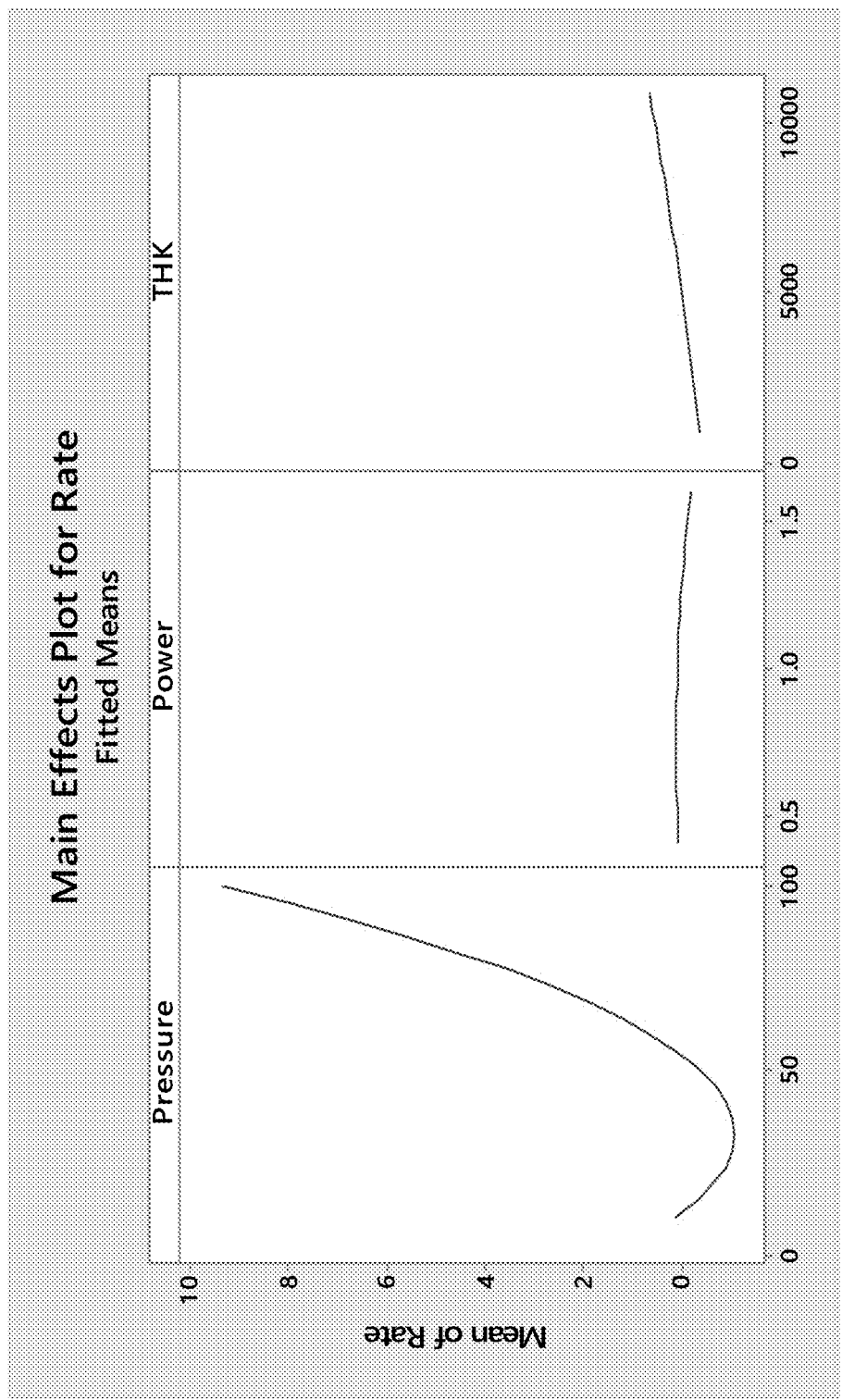
FIG. 12 is a plot of the mean of rate as a function of pressure, power, and gold thickness, according to one or more embodiments of the present invention.

FIG. 12 is a plot of the mean of the rate as a function of pressure, power, and gold thickness.

Figure 13:
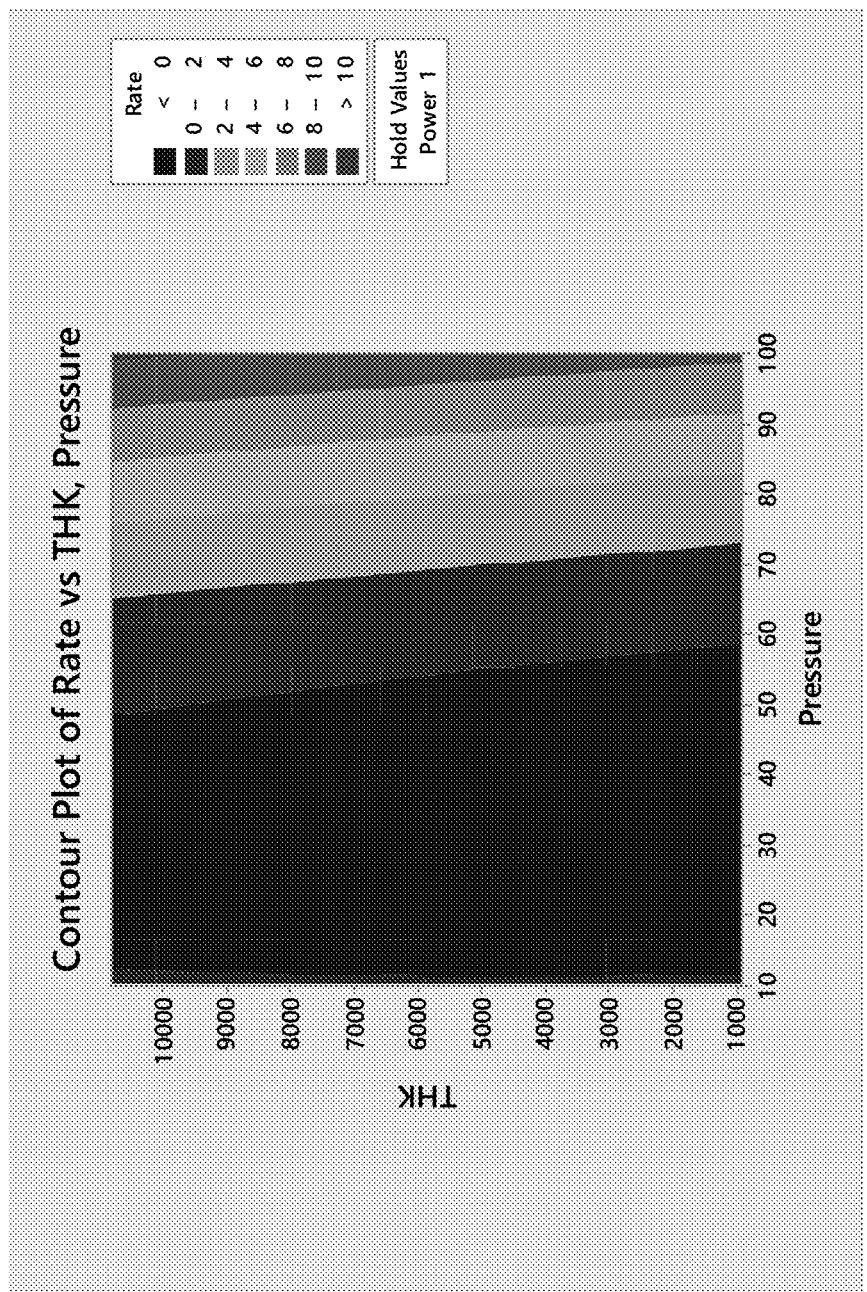
FIG. 13 is a contour plot of the rate versus thickness of the gold layer and pressure, according to one or more embodiments of the present invention.

FIG. 13 is a contour plot of the rate versus thickness of the gold layer and sputtering pressure.

The DOE analysis (FIG. 11, FIG. 12, and FIG. 13) show that pressure is the dominant factor in controlling adhesion when pillars 1004 are formed at the interface. Specifically, the analysis shows higher pressure and a thicker (e.g., gold) layer in the film achieve weaker adhesion, and sputtering power has little effect on adhesion. A lower temperature was found to provide weaker adhesion.

c. Effect of Two Layers of Gold on Adhesion

Figure 14:
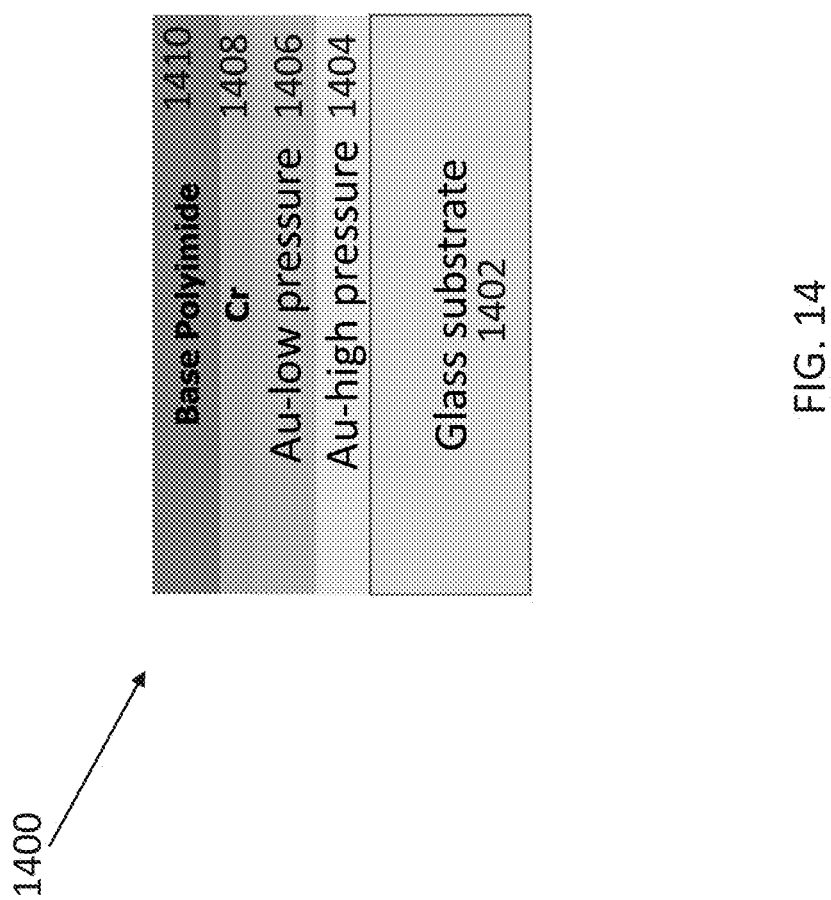
FIG. 14 illustrates another test sample comprising a layer stack on a glass substrate, according to one or more embodiments of the present invention.

FIG. 14 illustrates another test sample comprising a layer stack 1400 on a glass substrate 1402. The layer stack 1400 includes a first gold layer 1404 deposited using high pressure sputtering conditions on the glass substrate 1402, a second gold layer 1406 deposited using low pressure sputtering conditions on the first gold layer 1404, a chromium layer 1408 sputtered on the second Au layer 1406, and base polyimide layer 1410 deposited on the Cr layer 1408.

Following the previously discussed procedure, the marking patterns of FIG. 6B were then scratched into each of the films 1400 in the test samples using a knife or laser cutting. Table 2 compares the adhesion score for the sample 1400 with the double gold layer 1406, 1404 (sample 11) with the adhesion scores for samples 500 with a single gold layer 504 deposited at a low or high pressure (samples 1-10).

FIG. 15A illustrates the film 500 of the test sample of FIG. 6A comprising a gold layer 504 deposited using sputtering conditions including 100 mTorr pressure, 1.5 kW power, for a duration of 5 minutes. FIG. 15B illustrates the film 1400 of the test sample of FIG. 14 comprising a first gold layer 1404 deposited using sputtering conditions including 100 mTorr pressure, 1.5 kW power, for a duration of 5 minutes, and the second gold layer 1406 deposited using sputtering conditions including 4 mTorr pressure, 0.2 kW power, for a duration of 10 minutes. The results show that the test sample 1400 with the double gold layer (FIG. 14) has better adhesion than the sample 500 with one gold layer (FIG. 6A). Thus, the results unexpectedly and surprisingly show the combination of high/low-pressure gold layers 1404, 1406 can significantly affect the adhesion.

Figure 15E:
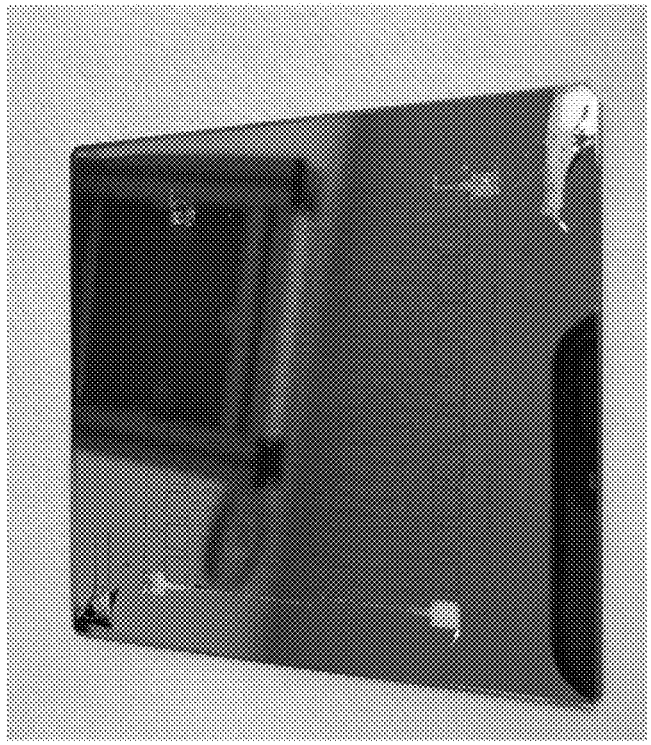
Figure 15D:
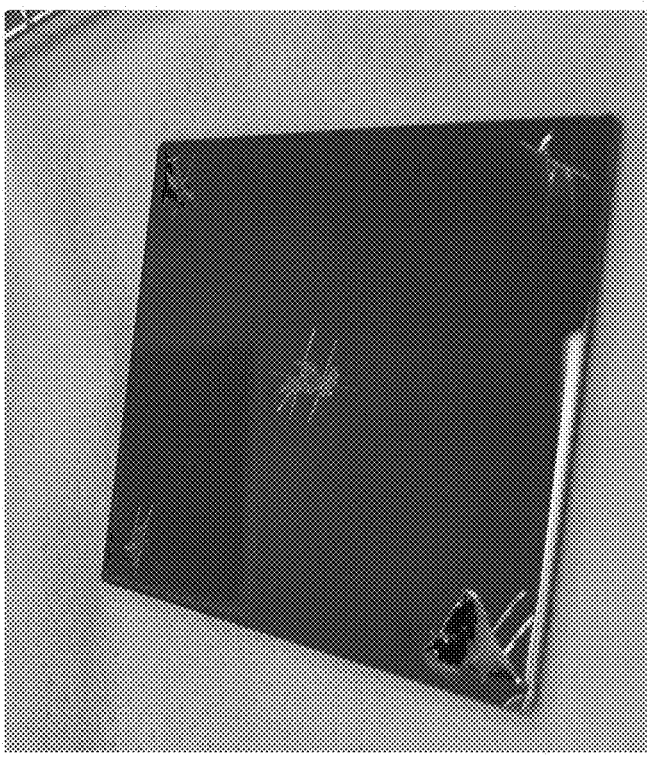

FIGS. 15C, 15D, and 15E illustrate the film 1400 with two gold layers 1404, 1406 deposited using the conditions for FIG. 15B has an adhesion that varies depending on position on the surface area. The adhesion uniformity may be increased by reducing defects and dust on the glass substrate and improving uniformity of deposition in the sputtering apparatus.

Example 3: Controlling Sputtering Rate

Figure 16:
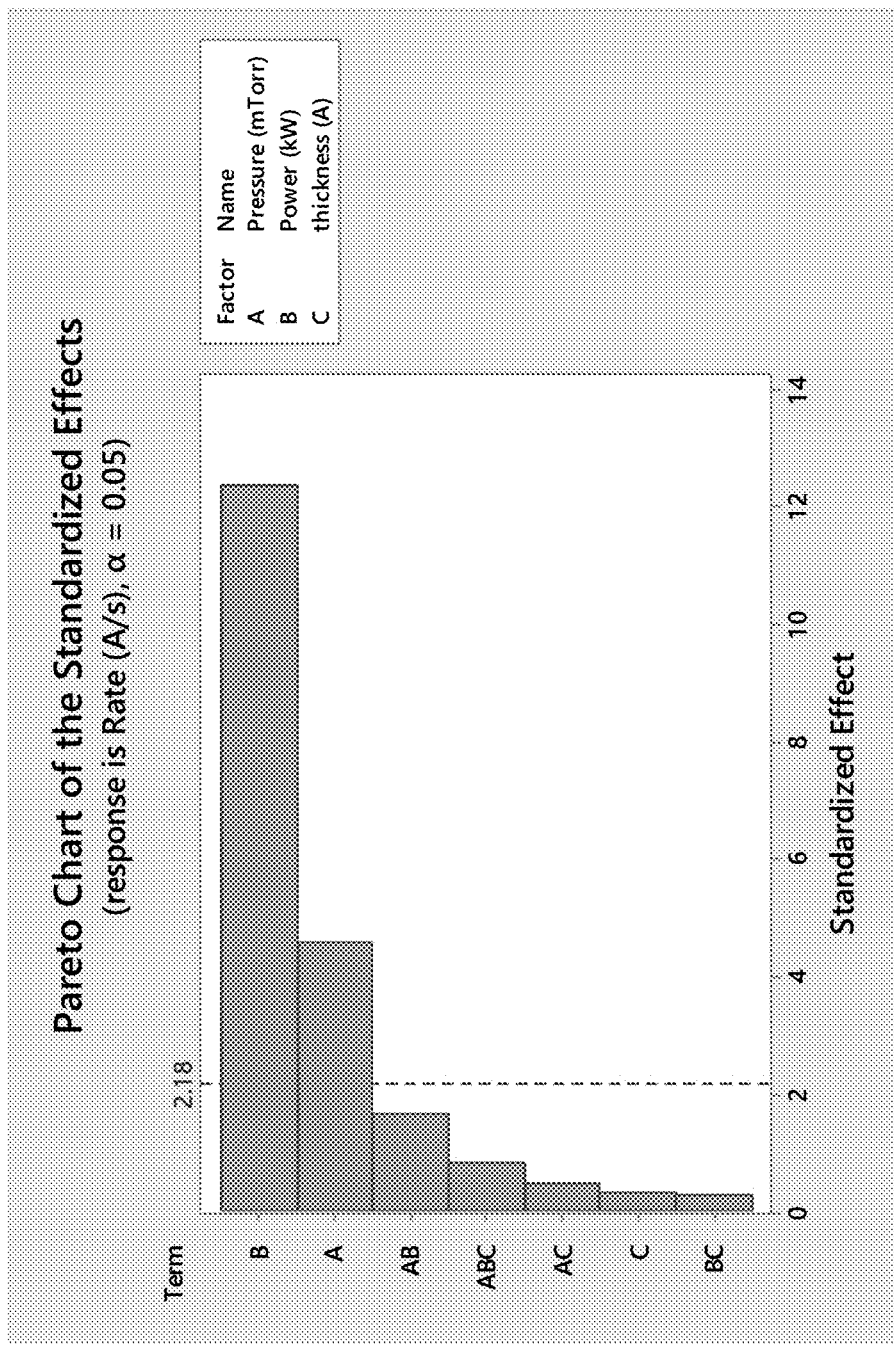
FIG. 16 illustrates a Pareto chart of the standardized effects of changing pressure, power, and gold thickness on sputtering rate, according to one or more embodiments of the present invention.

A DOE analysis was performed to determine the process parameters affecting sputtering rate of gold onto a glass substrate when no heat is applied. FIG. 16 illustrates a Pareto chart of the standardized effects of changing pressure, power, and gold thickness on sputtering rate, when no heat is applied. In the Pareto chart, response is the sputtering rate in Angstroms per second and $\alpha=0.05$.

Figure 17:
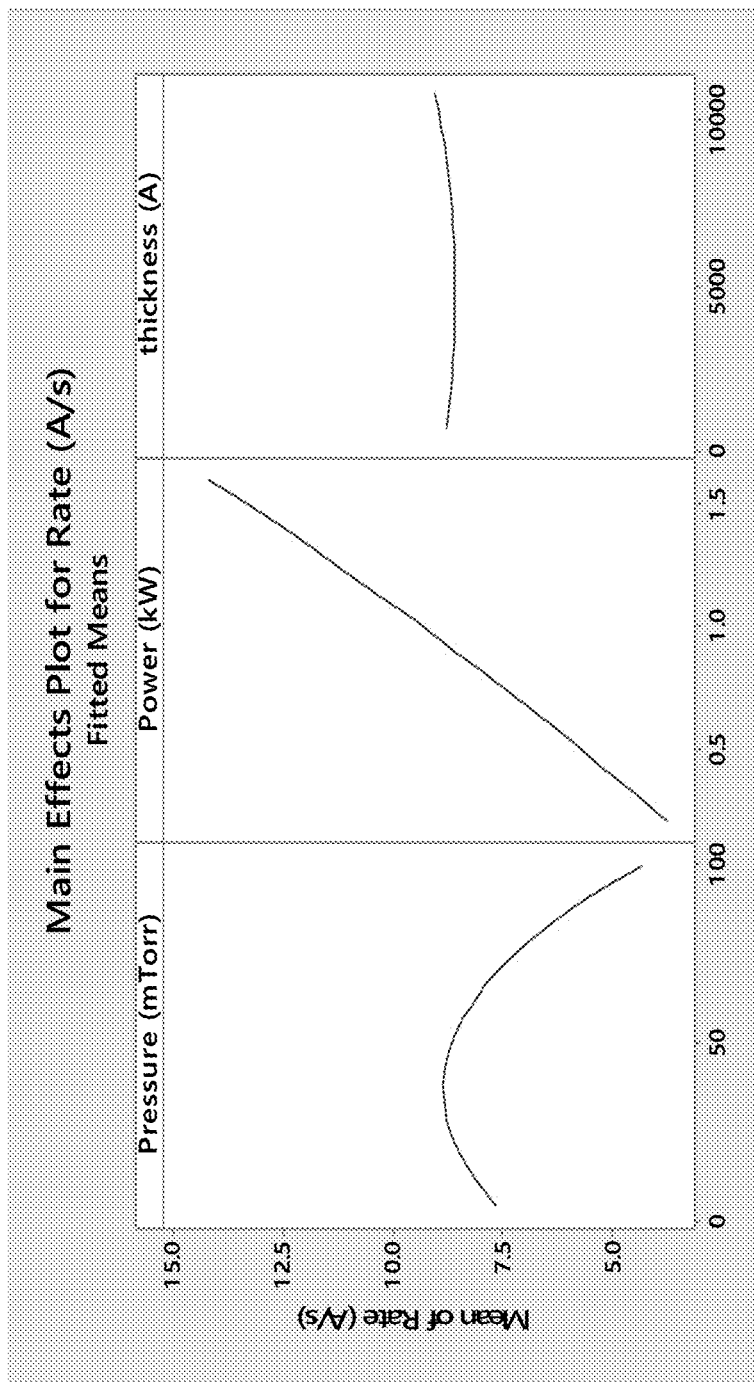
FIG. 17 is a plot of the mean of the sputtering rate as a function of pressure, power, and gold thickness, according to one or more embodiments of the present invention.

FIG. 17 is a plot of the mean of the sputtering rate as a function of pressure, power, and gold thickness.

Figure 18:
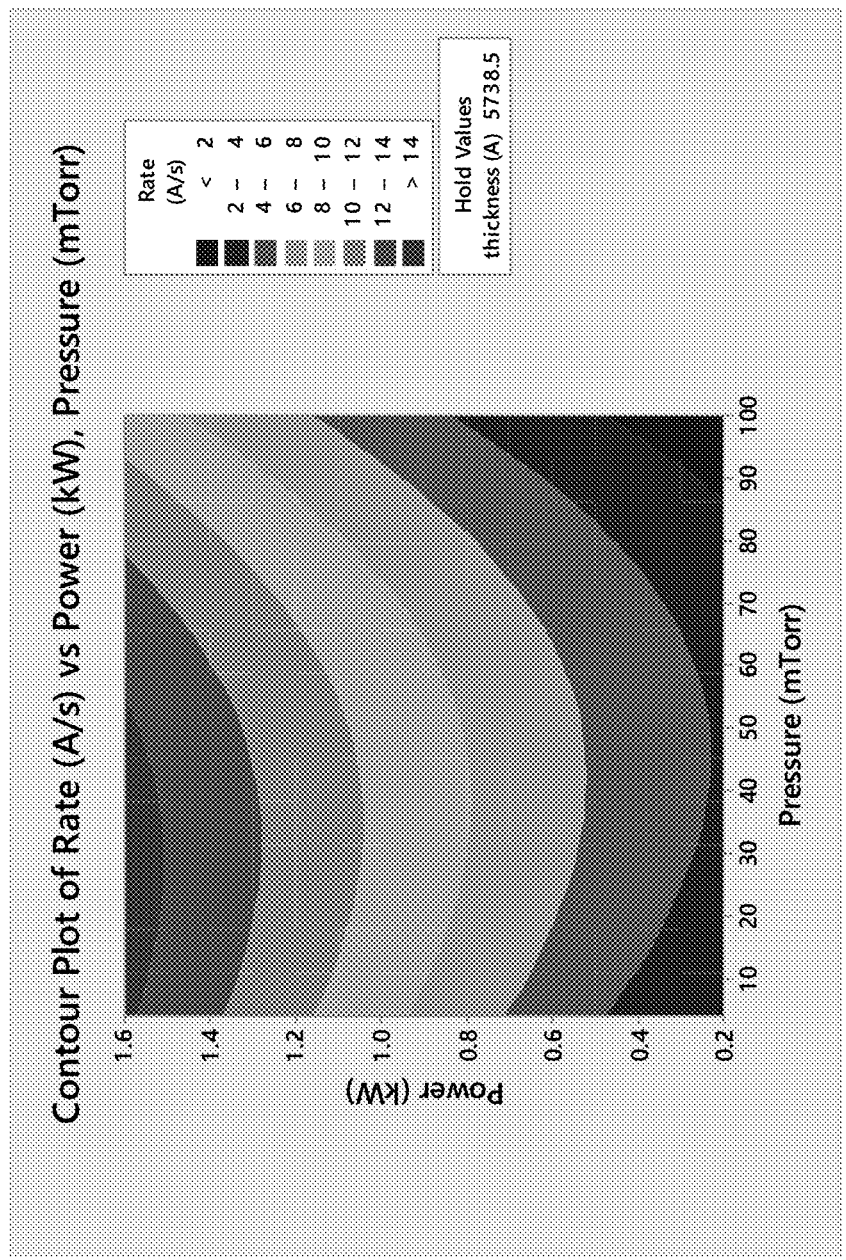
FIG. 18 is a contour plot of the sputtering rate versus sputtering power (kW) and pressure (mTorr), according to one or more embodiments of the present invention.

FIG. 18 is a contour plot of the sputtering rate versus sputtering power (kW) and pressure (mTorr).

The DOE analysis (FIG. 16, FIG. 17, and FIG. 18) shows that an optimal pressure exists for a maximum sputtering rate and that sputtering rate increases linearly with sputtering power. Thus, as illustrated herein, PVD conditions can be carefully selected to increase sputtering rate and control adhesion. In one or more embodiments, the DOE analysis is used to determine the sputtering parameters that achieve the fastest deposition rate and desired adhesion. Power and pressure may be used to control sputtering rate and adhesion.

Although the examples 2-4 refer to sputtering, the same results and findings (including adhesion control by properly selecting pressure) apply to deposition using PVD generally (e.g., including, but not limited to, electron beam deposition).

Example 4: Analyte Sensor Apparatus Fabrication

Figure 19:
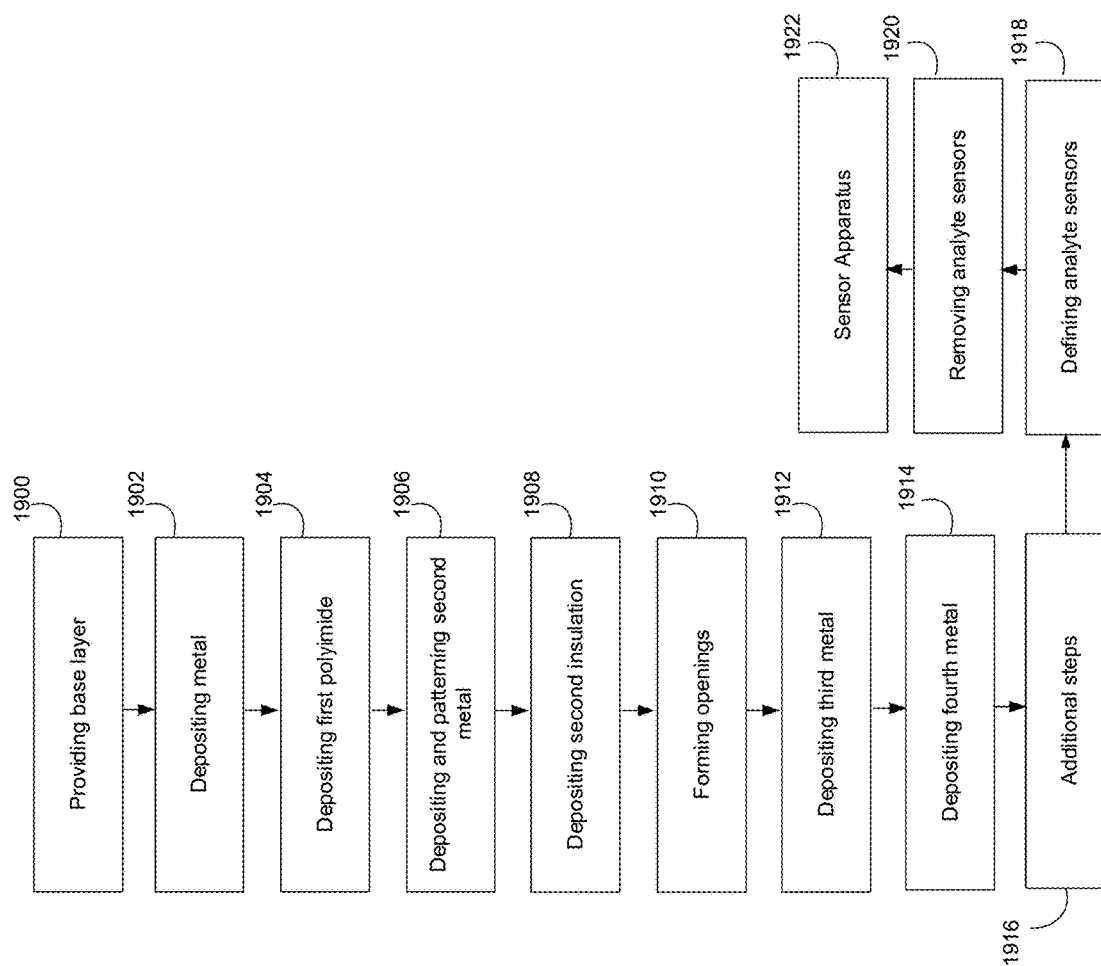
FIG. 19 is a flowchart illustrating a method of fabricating a sensor or sensor flex according to one or more embodiments of the present invention.
Figure 20:
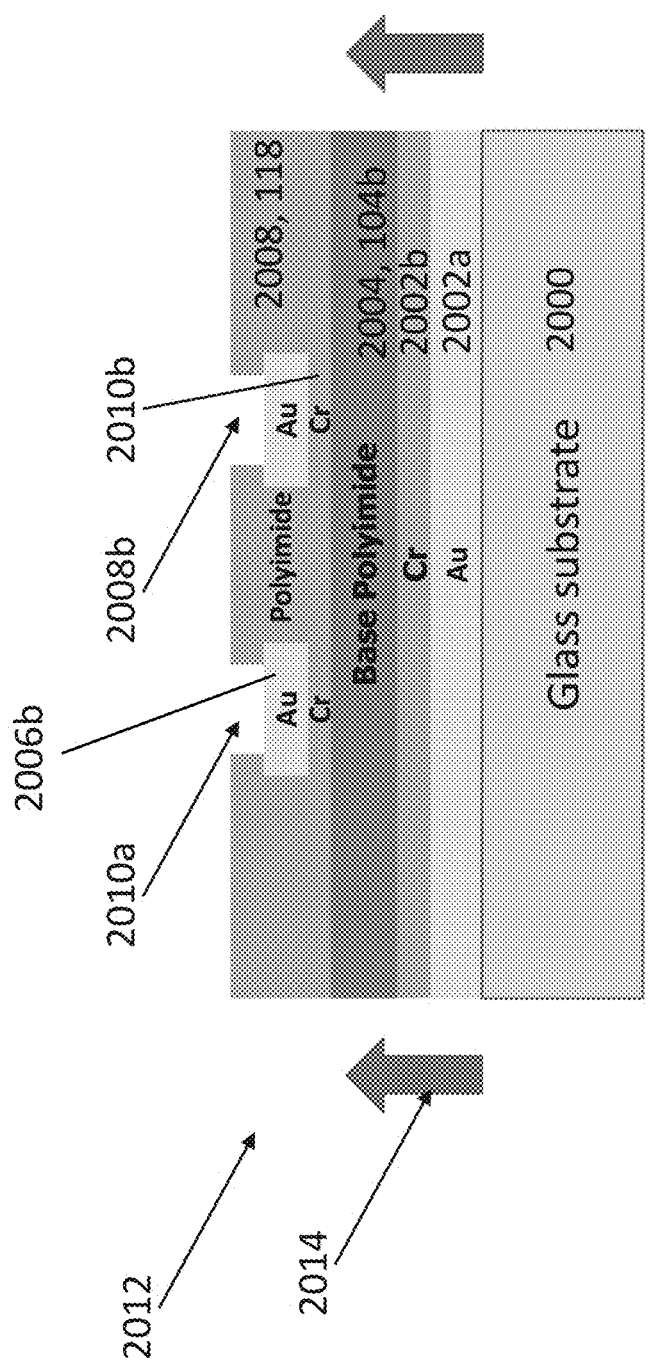
FIG. 20 illustrates fabrication of the backside counter electrode sensor embodiment using the PVD methods described herein.

FIG. 19, FIG. 20, and FIG. 1D illustrate a method of making an analyte sensor apparatus 100d.

Block 1900 represents providing a base (e.g., rigid) substrate 2000 (e.g., a glass substrate).

Block 1902 represents depositing metal 2002a, 2002b (physical vapor deposited metal) on the base substrate, e.g., using PVD. In one or more embodiments, the metal comprises a first layer 2002a (e.g., Au layer) on the base substrate 2000 and a second layer (e.g., Cr or Ti layer) 2002b on first Au layer 2002a. In one or more examples, the metal 2002a, 2002b extends laterally so as to form contact pads 110, 114.

Example PVD conditions include a pressure in a range of 2-250 mTorr, 70-100 mTorr, or 50-125 mTorr, a power in a range of 10 W-100 kW (e.g., 0.5 kW-2 kW, e.g., 0.8 kW) and a thickness of each of the metal layers in a range of at least 100 Angstroms (e.g., 1000-9000 Å). The PVD steps can comprise the pressure control steps described herein, e.g., the steps of Blocks 2600-2604 in FIG. 26 of Example 9. Example PVD processes include, but are not limited to, sputtering and electron beam deposition.

Block 1904 represents depositing a first insulation layer 2004 on the metal 2002a, 2002b. Example insulation layers include, but are not limited to, a polymer layer (such as, but not limited to, a polyimide).

Block 1906 represents depositing and patterning second metal 2006a, 2006b on the first insulation layer 2004, 104b. In one or more examples, second metal comprises a two layers—a second layer 2006b comprising Au on a first layer 2006b comprising Cr or Ti) and extends laterally so as to form contact pads 110, 114.

Block 1908 represents depositing a second insulation layer 2008, 118 onto the first insulation layer 2004 and the second metal 2006a, 2006b on the first insulation layer 2004. Example insulation layers include, but are not limited to, a polymer layer (such as, but not limited to, a polyimide).

Block 1910 represents forming a first opening 2010a and a second opening 2010b in the second insulation layer 2004 so as to expose second metal 2006b.

Block 1912 represents depositing third metal into the first opening 2010a and onto the second metal 2010b so as to form a working electrode WE (see FIG. 1D).

Block 1914 represents depositing fourth metal into the second opening 2010b and onto second metal 2006b so as to form a reference electrode (RE) (see FIG. 1D).

Block 1916 represents additional steps, including formation of openings in the second insulation layer 118 to expose the metal contact pads 110, 114b (referring to FIG. 1D) which comprise second metal 2006a, 2006b, and curing if necessary.

Block 1918 represents defining the analyte sensors in the film 2012 comprising the metal 2002a, 2002b, the second metal 2006a, 2006b, the first insulation layer 2004, 104b, the second insulation layer 2008, 118, and the electrodes WE, RE.

Block 1920 represents removing 2014 (e.g., peeling) the analyte sensors 100d from the base substrate 2000. In one or more embodiments, the step comprises removing (e.g., peeling) the physical vapor deposited metal 2002a, 2002b from the substrate 2000.

Block 1922 represents the end result, a sensor apparatus, e.g., as illustrated in FIG. 1D. The metal layers 2002a, 2002b, CE act as the backside counter electrode BCE as well as a layer for controlling adhesion to the base substrate 2000 using the pressure control methods described herein (see e.g., examples 2-3). Base polyimide layer 2004, 104b does not require patterning or etching to contact the BCE. In one or more examples, the method of Example 4 enables fabrication of a device comprising 1 flex with electrodes on both sides (as compared to a control device having interdigitated electrodes on one side as illustrated in FIG. 1F). As illustrated herein, a plurality (e.g., at least 36) of sensors 100d removed from the base substrate can all exhibit an ISIG of within 15% (see, e.g., FIG. 21D).

Example 5: Sits Results for Unity Sensor of Example 4

Figure 21A:
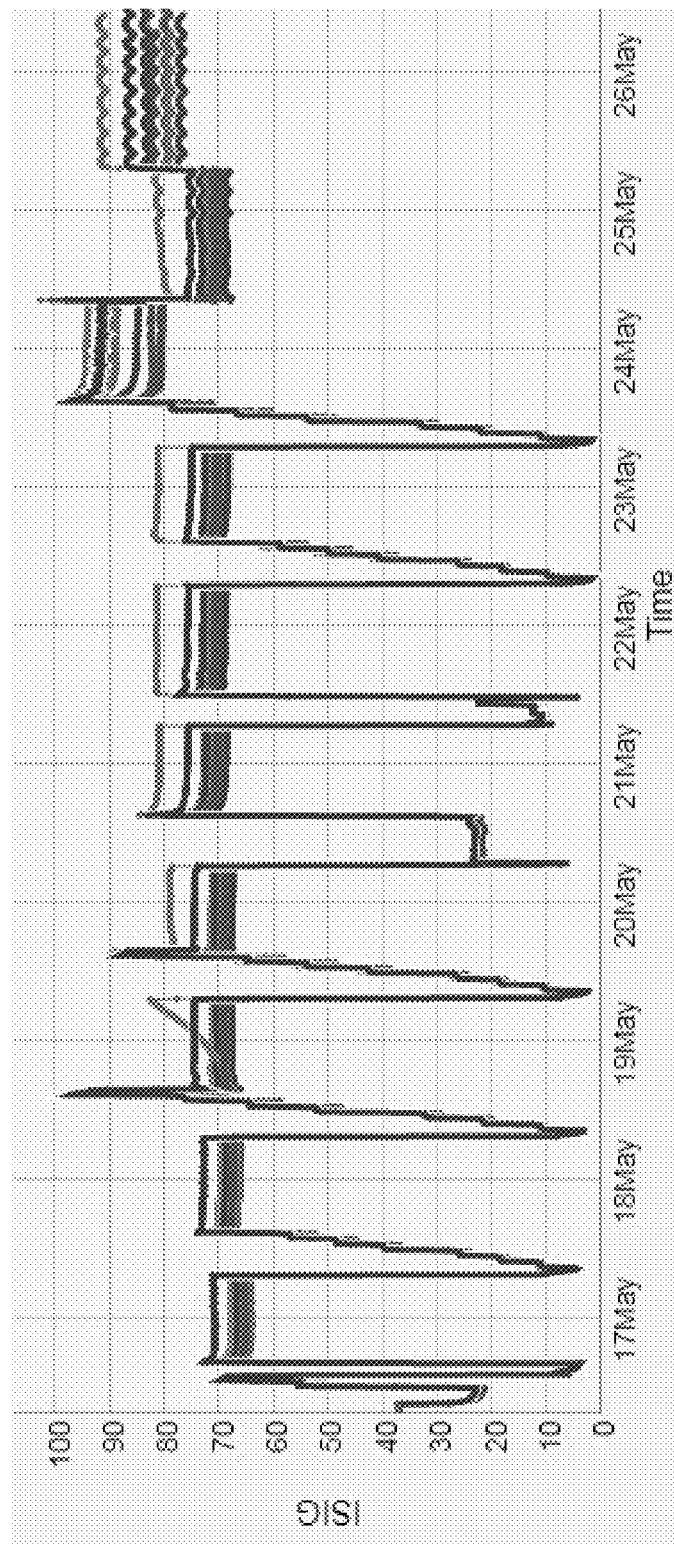
Figure 21B:
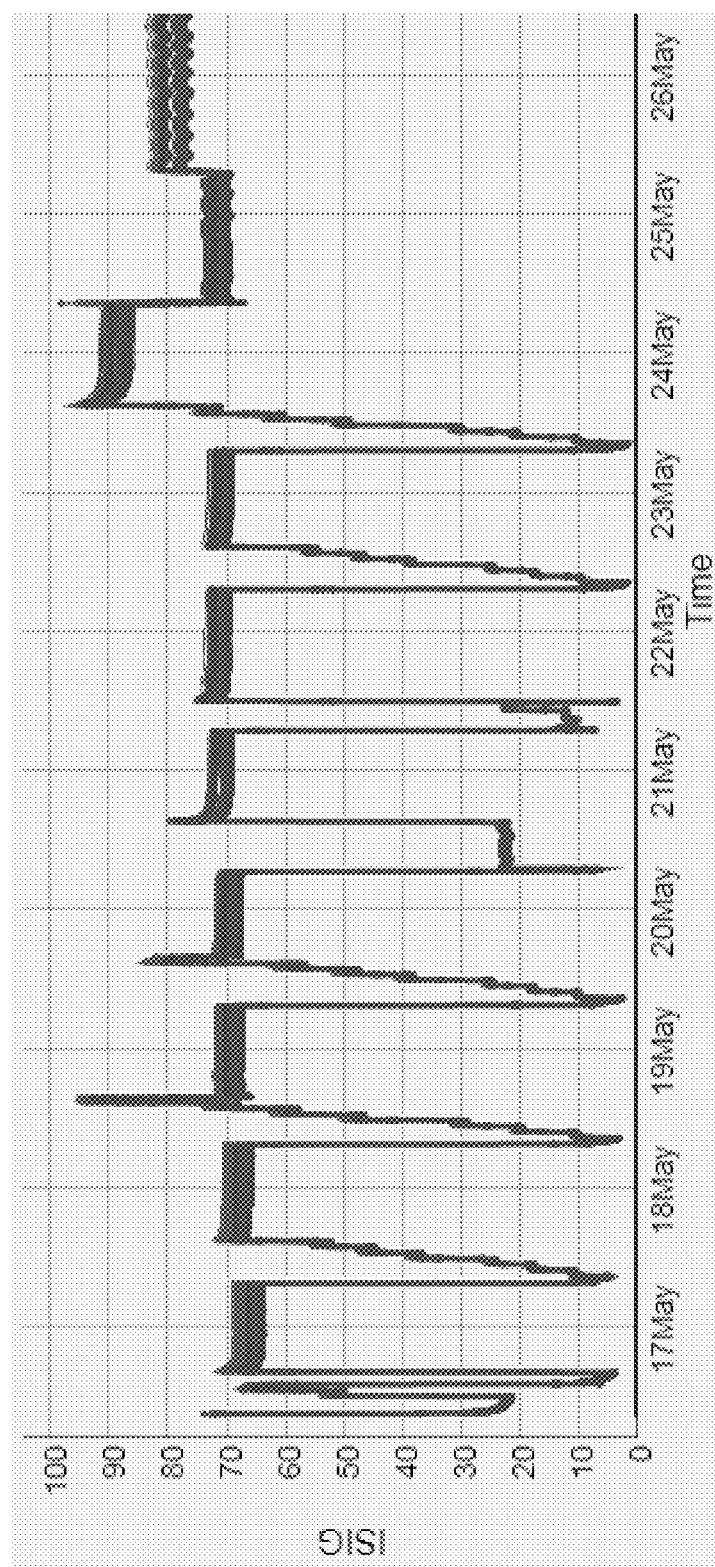

FIGS. 21A-21C illustrate SITS results for a control sensor as illustrated in FIG. 1F and FIG. 21D-21F illustrate the SITS results for the sensor of FIG. 1G (simulating/representing the performance of the device of FIG. 1D having a BCE fabricated using the method Example 4).

The sensor of FIG. 1G has two flexes:

Flex 1: nominal electrode E3 with tape over CE contact pad at the transmitter connection. The tape does not contact the body.

Flex 2: nominal E3 layer comprising base polyimide and nominal E3 electrode comprising Cr/Au and tape over WE & RE contact pad regions at the transmitter connection. This flex is a nominal E3 flex manufactured only through the metal sputtering process and the tape does not contact the body.

While the sensor of FIG. 1D has a single flex including the CE, the WE, and the RE, the performance of the FIG. 1D device is expected to be similar to the performance of the two flex FIG. 1G device because both the FIG. 1D device and the FIG. 1G device have a CE electrode on the backside on the opposite side from the WE.

TABLE 3

SITS summary for testing of the device of
FIG. 1D for 3 total SITS runs.

| SITS Run | Day 7/8 Isig Variablility (0.1% O2) Control | Day 7/8 Isig Variablility (0.1% O2) BCE | Long Term Stability (5% O2) Control | Long Term Stability (5% O2) BCE |
| --- | --- | --- | --- | --- |
| S3164 | 13.8 | 4.63 | 13.13% | 12.04% |
| S3166 | 11.95 | 7.49 | −0.37 | 1.86 |
| S3167 | 5.78 | 4.75 | 16.70% | 4.24% |

*indicates statistically significant difference.
The number of devices tested was n = 36 for the BCE device of FIG. 1D and n = 36 for the control device).

For the data in FIGS. 21A and 21B, the working electrode 132 and counter electrode 134 in the control sensor 130 comprise Pt, and the reference electrode in the control sensor 130 comprises Ag/AgCl; the WE in the sensor of FIG. 1G comprises Pt, the CE in the sensor of FIG. 1G comprises Au, and the RE in the sensor of FIG. 1D comprises Ag/AgCl.

The data in FIGS. 21D-21F and Table 3 for sensors tested in vivo on a pig illustrate improved long-term stability over the entire test, eliminated overnight Isig drift, and significantly (and surprisingly) less sensor to sensor variability (especially at low $O_2$ concentrations—stress conditions) for the BCE device of FIG. 1G (representing the device of FIG. 1D), as compared to the control sensor of FIG. 1F. In addition, the BCE of FIG. 1G did not exhibit major differences in temperature and AC responses, and there were no negative observations from visual inspection.

FIGS. 21C and 21F also show Vcounter (Vcntr) activity/movement in response to glucose sensing using the device of FIG. 1G is also surprisingly reduced as compared to for the control sensor of FIG. 1F. Moreover, the data shows Vcounter for the FIG. 1G sensor appeared more stable with a lower steady-state voltage.

Example 6: Analyte Sensor Apparatus Fabrication

Figure 22:
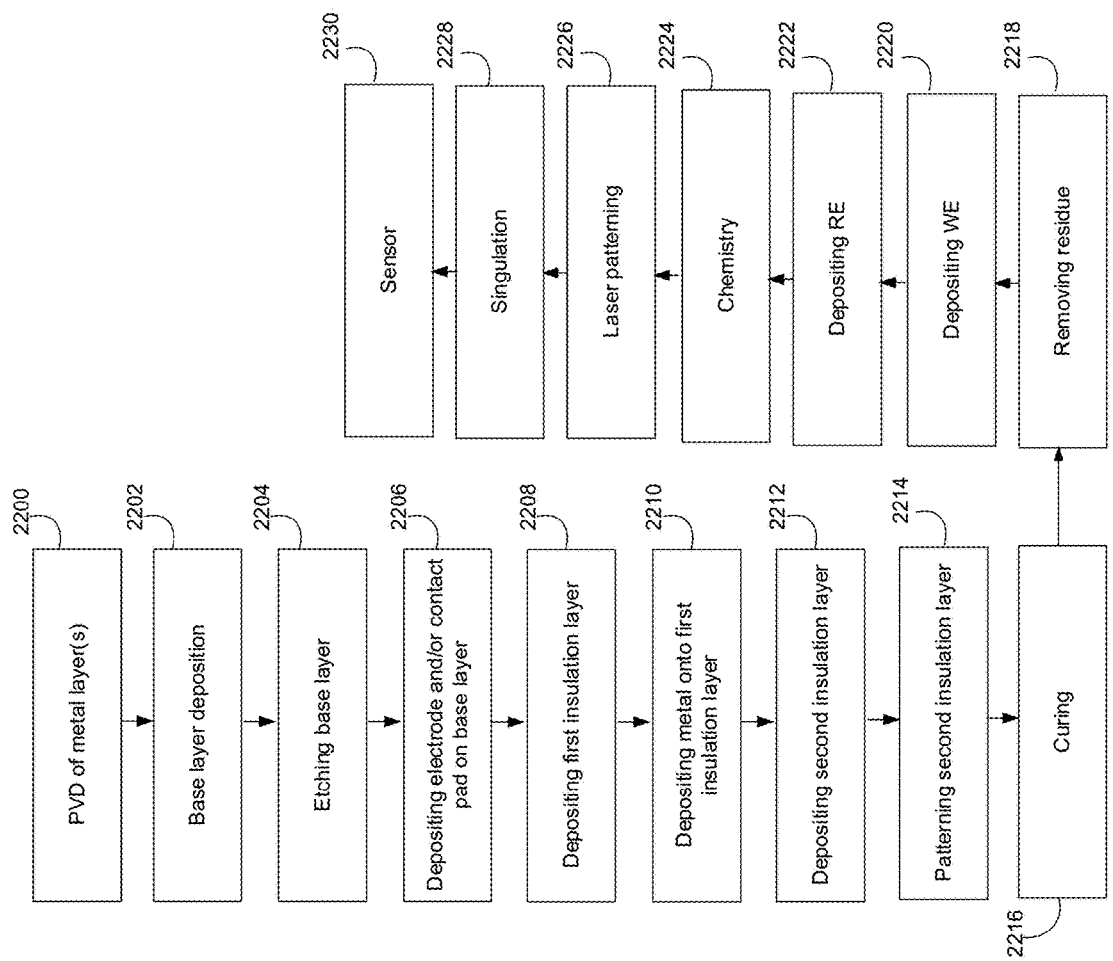
FIG. 22 is a flowchart illustrating a method of fabricating a sensor or sensor flex according to one or more embodiments of the present invention.

FIG. 22 is a flowchart illustrating a method of fabricating a glucose sensor or sensor flex (referring also to FIGS. 1A-1D and FIG. 23). The method comprises the following steps.

Block 2200 represents depositing one or more metal layers on a (e.g., rigid) substrate 2302 (e.g., glass) using physical vapor deposition (e.g., sputtering or electron beam deposition). Example metal layers 2300a, 2300b include, but are not limited to, Au, Cr, Ti and combinations thereof. In one or more embodiments, the layers 2300a, 2300b comprise one or more gold layers deposited on a glass substrate 2302 followed by deposition of Cr on the gold layer(s).

Example PVD conditions include a pressure in a range of 2-250 mTorr, 70-100 mTorr, or 50-125 mTorr, a power in a range of 10 W-100 kW (e.g., 0.5 kW-2 kW, e.g., 0.8 kW) and a thickness of each of the metal layers 2300a, 2300b of at least 100 Angstroms (e.g., 1000-9000 Å). The PVD steps can comprise the pressure control steps described herein, e.g., the steps of Blocks 2600-2604 in FIG. 26 of Example 9.

Block 2202 represents depositing a first or base layer 116 on the sputtered metal layer(s) 2300a, 2300b formed in Block 2200. Example base layers include, but are not limited to, a polymer layer (such as, but not limited to, a polyimide forming a first or base polyimide layer). In one or more embodiments, the step comprises spin casting the polymer (e.g., polyimide) onto the metal layer(s) 2300a, 2300b and then pre-curing the polymer (e.g., polyimide).

Block 2204 represents optionally patterning and/or etching the base layer 116 for deposition of one or more electrodes (e.g., WE and RE) and/or one or more contact pads 114. In one or more examples, the patterning comprises depositing a dry-etch mask (e.g., photoresist dry etch mask) on the base layer 116, dry etching the base layer 116 through openings in the dry-etch mask, and stripping the dry-etch mask from the base layer 116, thereby forming an etched pattern (including first opening) in the base layer 116.

Block 2206 represents depositing metal 112 (second metal) comprising the CE onto the etched pattern. Examples of the metal 112 include, but are not limited to, Au, Ti, and Cr and combinations thereof (e.g., Au and Ti and/or Cr). In one or more examples, the step comprises sputtering or electron beam depositing the metal 112 onto the base layer 116 including the etched pattern; depositing a mask (e.g., photoresist wet-etch mask) on the metal 112 deposited onto the base layer 116; etching (e.g., wet etching) the metal through openings in the mask; and stripping the mask from the metal 112.

Block 2208 represents depositing an insulation layer 104a (first insulation layer) on the base layer 116 and the metal on 112 the base layer 116. Example insulation layers include, but are not limited to, a polymer layer (such as, but not limited to, a polyimide forming a first insulation polyimide layer). In one or more examples, the insulation layer 104a is blanket deposited on the metal 112. In one or more further examples, the depositing comprises spin casting the insulation layer 104a so as to cover the base layer 116 and the metal 112; and pre-curing the insulation layer 104a.

Block 2210 represents depositing and patterning metal 108 (third metal) onto the first insulation layer 104a. Examples of metal include Au, Ti, and Cr and combinations thereof (e.g., Au and Ti and/or Cr). In one or more examples, the step comprises sputtering/e-beam depositing a film (e.g., thin film) of the metal 108 onto the first insulation layer 104a so as to blanket cover the first insulation layer 104a; depositing a mask (e.g., photoresist wet-etch mask) on the metal sputtered onto the first insulation layer 104a etching (e.g., wet etching) the metal through openings in the mask; and stripping the mask from the metal 108.

Block 2212 represents depositing a second insulation layer 118 on the first insulation layer 104a and the metal 108 on the first insulation layer 104a. Example second insulation layers include, but are not limited to, a polymer layer (such as, but not limited to, a polyimide forming a second insulation polyimide layer). In one or more examples, the step comprises spin casting the second insulation layer 118 onto the first insulation layer 104a and the metal 108 on the first insulation layer 104a; and pre-curing the second insulation layer 118.

Block 2214 represents patterning the second insulation layer 118, e.g., using photolithography, and forming an etched pattern in the second insulation layer 118 comprising a second well or second opening 2304 and a third well or third opening 2306.

Block 2216 represents optionally performing a final cure of the structure formed in blocks 2200-2214.

Block 2218 represents optionally removing residue from the second insulation layer 118, e.g., using $O_2$.

Block 2220 represents depositing metal (fourth metal) and other layers needed to form the WE. In one or more embodiments, the step comprises depositing metal pillars 124 into the second well/opening 2304 formed in the second insulation layer 118. Examples of metal pillars include, but are not limited to, platinum or gold pillars. In one or more embodiments, the step comprises depositing a photoresist lift off mask in the first well 2304; performing a cleaning (e.g., O$_2$ plasma descum) of the photoresist lift off mask; sputtering metal into openings in the mask so as to form the metal pillars 124 extending through the openings from the exposed surface of the metal 108 in the first well 2304; and lifting off/removing the mask, leaving the pillars 124 on the metal 108.

Block 2222 represents depositing metal (fifth metal) into the third well/opening 2306 so as to form the reference electrode (RE) in the third well or third opening 2306. Examples of deposition methods include, but are not limited to, depositing the metal using electroplating or screen printing. Example metal for the RE comprises, but is not limited to, Pt, gold, and Cr.

Block 2224 represents performing a chemistry step, wherein additional chemically active layers/constituents are deposited on the WE (e.g., onto the pillars) so that the WE has the proper functionality in a glucose sensor. Example constituents include, but are not limited to, one or more of an interference rejection constituent, an analyte sensing constituent 410, a protein constituent 416, an adhesion promoting layer 414, and an analyte modulating layer 412, and/or cover layer as described herein.

Block 2226 represents processing the structure into individual sensors 100, e.g., by cutting or laser patterning.

Block 2228 represents singulation or removing (e.g., peeling) the individual analyte sensors 100a-d from substrate 2302. In one or more embodiments, the PVD methods described herein directed to adhesion control enable singulation of the flex or sensor 100a-d from the substrate 2302 (e.g., glass) without damaging the CE and the contact pads 110, 114. In one or more embodiments, the step comprises removing (e.g., peeling) the physical vapor deposited metal 2300a, 2300b from the (e.g., rigid) substrate 2002.

Block 2230 represents the end result, an analyte sensor apparatus 100a-d, such as a glucose sensor, as illustrated in FIGS. 1A-1D. FIGS. 1A-1D illustrate various double-sided single flex sensor embodiments accommodating multiple electrodes and including electrodes on both sides of the sensor flex 100a-d, and wherein components of the sensor 100a-d are flexible so as to form a flexible sensor (sensor flex). The flex or sensor 100a-100d includes the WE and RE on the top side of flex or sensor and a CE on the backside of the flex or sensor. In one or more embodiments, a smooth CE is formed on the backside 102b and has enough surface area to balance the electrochemical reaction occurring at the WE. However, in one or more examples, no chemistry needs to take place on the backside 102b of the flex or sensor 100a-d. Extra electrodes (not shown) may also be included for a background sensor or differential sensor etc., and the electrodes may interface with a transmitter connection scheme. The device 100a-d can be used in the potentiostat circuit of FIG. 3.

In one or examples, the fabrication method described herein may increase the working electrode area, prevent the "drift" effect and/or simplify the manufacturing process.

Investigation of the process parameters has found excellent process control, design control and repeatability. The process is a high throughput process and easily transferable between plates and 8" wafer.

Example 7: Method of Depositing a Film and Controlling Adhesion

FIG. 24 is a flowchart illustrating a method of depositing films on a substrate. The method comprises the following steps.

Block 2400 represents controlling pressure of a gas in a chamber used for depositing metal using physical vapor deposition (PVD). In one or more examples, the step additionally comprises controlling at least one additional PVD parameter selected from thickness of the metal, a number of layers of the metal, and a power used during the physical vapor deposition.

Block 2402 represents depositing the metal on a substrate using physical vapor deposition (PVD).

Block 2404 represents depositing a film on the metal.

Block 2406 represents measuring the degree of adhesion of the film to the substrate as a function the at least one PVD parameter (including pressure). In one or more embodiments, the measuring comprises assigning an adhesion score.

Example PVD conditions include a pressure in a range of 2-250 mTorr, 70-100 mTorr, or 50-125 mTorr, a power in a range of 10 W-100 kW (e.g., 0.5 kW-2 kW, e.g., 0.8 kW) and a thickness of each of the metal layers in a range of at least 100 Angstroms (e.g., 1000-9000 Å).

Block 2408 represents optionally determining the pressure or other PVD parameter that achieves a desired adhesion of the film to the substrate. In one or more examples, the step comprises analyzing the degree of adhesion as a function of the at least one physical vapor deposition parameter so as to determine the relative impact of the at least one physical vapor deposition parameter on the degree of adhesion. In one or more examples, the analyzing comprises performing a design of experiments (DOE) analysis; and plotting the degree of adhesion as a response in a Pareto chart. The adhesion score and determining/analyzing steps of block 2408 may be performed in a processor or computer using a computer-readable program code having instructions, which when executed, cause the processor or computer to perform a statistical analysis of the measurements obtained in Block 2406, thereby determining the PVD parameter that achieves the desired adhesion.

Example 8: Method of Making a Device

FIG. 25 is a flowchart illustrating a method of depositing of a film or making a device on a substrate. The method comprises the following steps.

Block 2500 represents placing a substrate (e.g., rigid substrate) in a physical vapor deposition (PVD) (e.g., sputtering) chamber.

Block 2502 represents setting a PVD conditions including pressure of a gas in the chamber used for depositing material using PVD. In one or more examples, the pressure is determined using the methods described in Example 7.

Block 2504 represents depositing PVD metal on the substrate using the physical vapor deposition at the pressure.

In one or more embodiments, the metal comprises a plurality of layers each deposited at a different pressure.

In one or more embodiments, the PVD comprises sputtering or electron beam deposition, including ionizing the gas so as to form ionized gas particles; and accelerating the ionized gas particles onto a target comprising the metal using an electric and/or magnetic field having a power in a range of, e.g., 10 Watts-100 kW (e.g., 0.5 kilowatts to 2 kilowatts). In one or more examples, the pressure of the gas is in a range of 2-250 mTorr, 70-100 mTorr, or 50-125 mTorr. In one or more embodiments, the PVD metal comprises one or more layers each having a thickness in a range of at least 100 Angstroms, e.g., 1000-9000 Å. In one or more examples, the PVD metal comprises a first layer deposited on the substrate at the pressure in a range of 50-250 mTorr (or 5-150 mTorr) and a second layer deposited on the first layer at the pressure in a range of 2-50 mTorr or 2-30 mTorr).

In one or more embodiments, the PVD deposited metal includes at least one structured layer selected from a patterned layer, a roughened layer, a non-uniform layer, a layer including voids, and a layer comprising pillars.

Block 2506 represents depositing a film or device structure on the metal, e.g., as described in Examples 4 and 6. The pressure selected in Block 2602 may be associated with a pre-determined adhesion of the film to the substrate, the pre-determined adhesion allowing (1) processing of the film into a device while the film is adhered to the substrate; and (2) removal (e.g., peeling) of the device from the substrate.

Block 2508 represents optionally processing the film into one or more devices. In one or more examples, the processing comprises patterning or cutting the film.

Block 2510 represents optionally peeling or removing the devices from the substrate.

Block 2512 represents the end result, a device, e.g., as illustrated in FIGS. 1A-1D. In one or more embodiments, the device comprises an exposed surface S of PVD metal 2302a, 2302b, 2002a, 2002b peeled/removed from a rigid substrate 2000, 2302. Example devices include, but are not limited to, a device including a microelectromechanical (MEMS) device structure, an optoelectronic device structure, a circuit, a battery electrode, a fuel cell electrode, or an electrode CE having an electrochemically active surface 122. Microarrays and multielectrode arrays may be fabricated.

As illustrated herein, investigation of the process parameters has found excellent process control, design control and repeatability. The process is a high throughput process and easily transferable between plates and 8" wafer.

In one or more examples, a separation D, arrangement, or configuration of the working electrode WE and the counter electrode CE in an analyte sensor apparatus 100a-100e is such that, in response to a constant analyte concentration, the electrical current (ISIG) varies by less than 15% over a period of 31 days and/or the chemical products created by the working and counter electrode reactions do not interfere or have detrimental interactions with the performance of the electrodes (WE, CE) (see FIGS. 21D-21F).

In one or more examples, in a set of at least 36 of the sensors 100a-100e fabricated using the methods described herein, a separation D, arrangement, configuration, and electroactivity of the working electrode WE and the counter electrode CE in each of the sensors 100a-100e is such that, in response to the same analyte concentration, the electrical currents (ISIG) outputted by each of the sensors are within 15% (see FIGS. 21D-21F).

In one or more embodiments, the PVD apparatus is coupled to a processor or computer using a computer-readable program code having instructions, which when executed, cause the processor or computer to control the PVD deposition parameters in PVD apparatus, so as to achieve a desired adhesion of the film to the substrate.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The descriptions and specific examples, while indicating some embodiments of the present invention are given by way of illustration and not limitation. Many changes and modifications within the scope of the present invention may be made without departing from the spirit thereof, and the invention includes all such modifications.

What is claimed is:

1. A method of making a plurality of devices, comprising:
    placing a substrate in a physical vapor deposition (PVD) chamber;
    setting a pressure of a gas in the PVD chamber, wherein the pressure is in a range of 2-250 millitorr (mTorr);
    depositing metal on the substrate in the PVD chamber using sputtering at the pressure so that the metal is in direct contact with the substrate and the metal comprises the metal comprises at least one structured layer comprising pillars; and
    depositing a film on the metal;
    processing, including cutting, the film into the plurality of devices while the film is adhered to the substrate, wherein the processing further comprises cutting the metal so that each of the devices comprise a portion of the metal; and
    removing each of the devices from the substrate after the cutting, wherein the devices each comprise a sensor including the portion of the metal comprising an electrode used for sensing a concentration of an analyte in an in-vivo environment in contact with the electrode, and
    wherein the portion of the metal comprises an exposed surface of the sensor.

2. The method of claim 1, wherein the PVD comprises:
    ionizing the gas so as to form ionized gas particles; and
    accelerating the ionized gas particles onto a target comprising the metal using an electric and/or magnetic field and a power in a range of 10 W to 100 kilowatts.

3. The method of claim 2, wherein the metal comprises a layer having a thickness of at least 100 Å.

4. The method of claim 2, wherein the metal comprises a layer having a thickness in a range of 600-1500 Å.

5. A plurality of the devices made using the method of claim 1.

6. The method of claim 1, wherein the devices each comprise a circuit and the electrode having an electrochemically active surface.

7. The method of claim 1, wherein:
    wherein the cutting comprises cutting along a line surrounding each of the devices on the substrate; and
    the removing comprises peeling each of the devices from the substrate.

8. The method of claim 1, wherein the pressure is determined using a method comprising:
    measuring a degree of adhesion of the film to the substrate as a function of the pressure used during the PVD; and
    determining the pressure that achieves the adhesion of the film to the substrate that allows lifting of the metal.

9. The method of claim 8, further comprising:
    measuring the degree of adhesion as a function of a plurality of PVD parameters including the pressure and other PVD parameters including at least one of a power used during the PVD, a number of layers of the metal, a deposition rate, and a thickness of the metal, so as to determine a relative impact of the pressure, as compared to the other PVD parameters, on the degree of adhesion; and selecting the pressure as a function of the other PVD parameters and so as to achieve the desired adhesion that allows the lifting of the metal.

10. The method of claim 8, further comprising:

controlling at least one PVD parameter selected from thickness of the metal, a number of layers of the metal, and a power used during the PVD;

measuring the degree of adhesion of the film to the substrate as a function the at least one PVD parameter; and depositing the film using the at least one PVD parameter and the pressure achieving the adhesion.

11. The method of claim 1, wherein:

the sensor comprises an analyte sensing layer on a working electrode; and the analyte sensing layer detectably alters an electrical current at the working electrode in a presence of the analyte.

12. The method of claim 11, wherein the analyte comprises glucose and the sensor is a glucose sensor.

13. The method of claim 1, wherein the electrode comprises a counter electrode.

14. The method of claim 13, further comprising depositing a working electrode and an insulating layer, wherein:

the sensor comprises the counter electrode on a backside of the sensor; and an insulating layer is between the working electrode and the counter electrode.

* * * * *